(12) United States Patent
Tai

(10) Patent No.: US 8,778,302 B2
(45) Date of Patent: Jul. 15, 2014

(54) PROCASPASE 8-MEDIATED DISEASE TARGETING

(75) Inventor: Isabella Tai, Vancouver (CA)

(73) Assignee: The University of British Columbia, Vancouver, BC (CA)

( * ) Notice: Subject to any disclaimer, the term of this patent is extended or adjusted under 35 U.S.C. 154(b) by 1215 days.

(21) Appl. No.: 12/530,504

(22) PCT Filed: Mar. 7, 2008

(86) PCT No.: PCT/CA2008/000460
§ 371 (c)(1),
(2), (4) Date: Jul. 10, 2010

(87) PCT Pub. No.: WO2008/109997
PCT Pub. Date: Sep. 18, 2008

(65) Prior Publication Data
US 2010/0272643 A1 Oct. 28, 2010

Related U.S. Application Data

(60) Provisional application No. 60/905,807, filed on Mar. 9, 2007, provisional application No. 60/960,305, filed on Sep. 25, 2007.

(51) Int. Cl.
*A61K 51/00* (2006.01)
*A61M 36/14* (2006.01)
*A61K 38/43* (2006.01)
*A61K 49/00* (2006.01)
*C07K 14/00* (2006.01)

(52) U.S. Cl.
CPC . *A61K 38/43* (2013.01); *A61K 3/16* (2013.01); *A61K 49/0056* (2013.01); *C07K 14/00* (2013.01)
USPC ......... 424/1.69; 424/1.11; 424/1.65; 514/1.1; 514/21.2; 514/21.3; 530/300

(58) Field of Classification Search
CPC ...... B65D 85/00; A61B 10/007; A61B 10/00; A61B 10/0041; A61B 10/0045; A61B 10/0096; A61K 2123/00; A61K 2121/00; A61K 51/02; A61K 51/088; A61K 51/0497; A61K 51/00; A61K 51/04; A61K 51/06; A61K 51/08; A61K 38/00; A61K 38/02; A61K 38/16; A61K 38/43; A61K 49/0002; A61K 49/0004; A61K 49/00; A61K 49/001; A61K 49/0052; A61K 49/0054; A61K 49/0056; C07K 2/00; C07K 14/00
USPC ........... 424/1.11, 1.65, 1.69, 1.81, 1.85, 1.89, 424/9.1, 9.3, 9.4, 9.5, 9.6, 9.7, 9.8; 514/1, 514/1.1, 21.2, 21.3; 530/300, 324, 350; 206/223, 569, 570
See application file for complete search history.

(56) References Cited

U.S. PATENT DOCUMENTS 7,354,736 B2 * 4/2008 Wallach et al. .............. 435/69.1

FOREIGN PATENT DOCUMENTS

| CA | 2 399 255 | 8/2001 |
| CA | 2 593 648 | 7/2006 |
| WO | WO 01/62300 | 8/2001 |
| WO | WO 2006/074451 | 7/2006 |
| WO | WO 2007/070708 | * 6/2007 |
| WO | WO 2008/000079 | 1/2008 |

OTHER PUBLICATIONS

Golub et al., Science, Oct. 15, 1999, pp. 531-537.*

* cited by examiner

*Primary Examiner* — D L Jones
(74) *Attorney, Agent, or Firm* — Saliwanchik, Lloyd & Eisenschenk

(57) ABSTRACT

The invention provides compositions and method for delivering a therapeutic or diagnostic agent to a disease site in a mammal, the method comprising administering to the mammal a therapeutically or diagnostically effective amount of a pharmaceutical composition, wherein the pharmaceutical composition comprises the therapeutic or diagnostic agent coupled to a Procaspase 8 polypeptide and a pharmaceutically acceptable carrier.

26 Claims, 22 Drawing Sheets

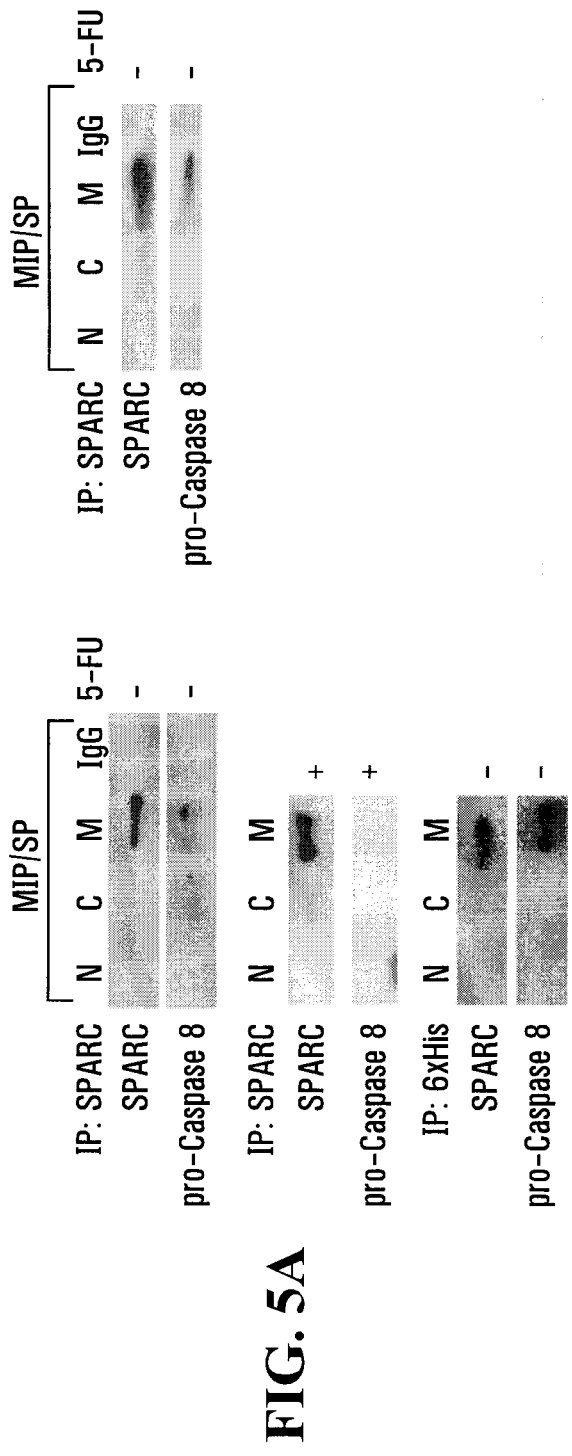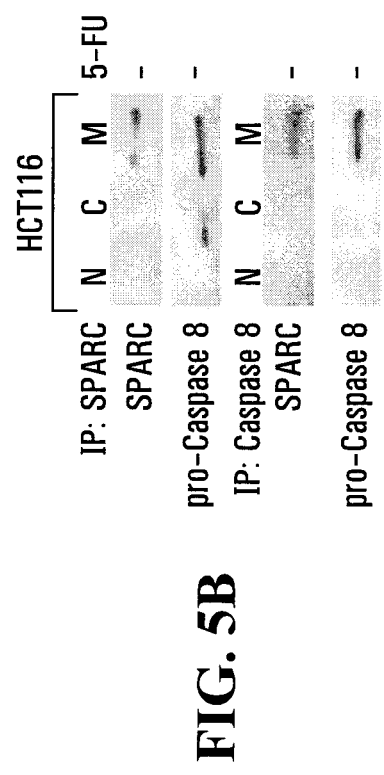
FIG. 5A
FIG. 5B

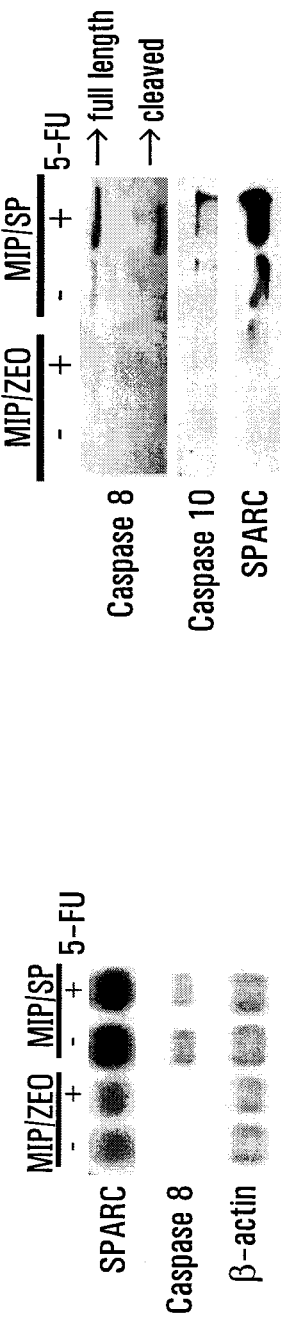

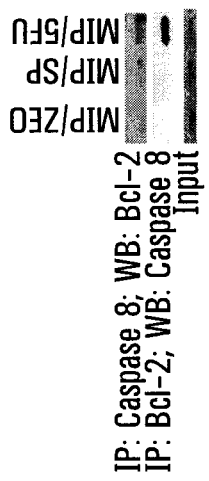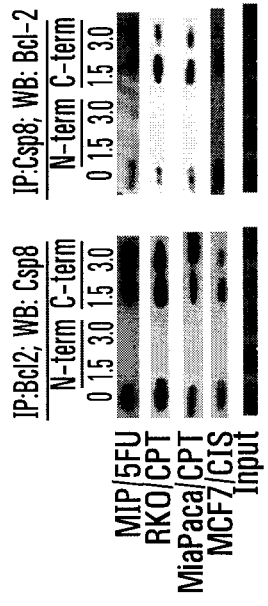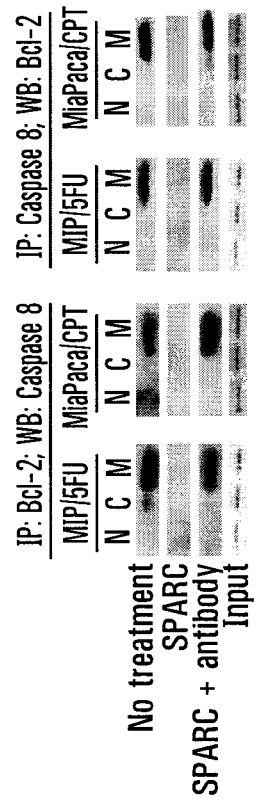
FIG. 9A
FIG. 9B
FIG. 9C

PROCASPASE 8-MEDIATED DISEASE TARGETING

This application is a National Stage Application of International Application Number PCT/CA2008/000460, filed Mar. 7, 2008; which claims the benefit of U.S. Provisional Application Ser. No. 60/905,807, filed Mar. 9, 2007 and U.S. Ser. No. 60/960,305, filed Sep. 25, 2007, which are incorporated herein by reference in their entirety.

BACKGROUND OF THE INVENTION

Secreted Protein, Acidic, Rich in Cysteines (SPARC), also known as osteonectin, is a 281 amino acid glycoprotein which is expressed in the human body.

The expression of SPARC is developmentally regulated, with SPARC being predominantly expressed in tissues undergoing remodeling during normal development or in response to injury. See, e.g., Lane et al., FASEB J., 8, 163-173 (1994). For example, high levels of SPARC protein are expressed in developing bones and teeth, principally osteoblasts, odontoblasts, perichondrial fibroblasts, and differentiating chondrocytes in murine, bovine, and human embryos. SPARC also plays important roles in cell-matrix interactions during tissue remodeling, wound repair, morphogenesis, cellular differentiation, cell migration, and angiogenesis, including where these are associated with disease states. For example, SPARC is expressed in renal interstitial fibrosis, and plays a role in the host response to pulmonary insults, such as bleomycin-induce pulmonary fibrosis.

SPARC also is upregulated in several aggressive cancers, but is absent from the vast majority of normal tissues. See, e.g., Porter et al., J. Histochem. Cytochem., 43, 791 (1995) and other references identified below. Indeed, SPARC expression is induced among a variety of tumors (e.g., bladder, liver, ovary, kidney, gut and breast). For example, in bladder cancer, SPARC expression has been associated with advanced carcinoma, with invasive bladder tumors of stage T2 or greater being shown to express higher levels of SPARC relative to bladder tumors of stage T1 (or less superficial tumors). See, e.g., Yamanaka et al., J. Urology, 166, 2495-2499 (2001). In meningiomas, SPARC expression has been associated with invasive tumors only. See, e.g., Rempel et al., Clincal Cancer Res., 5, 237-241 (1999). SPARC expression also has been detected in 74.5% of in situ invasive breast carcinoma lesions (see, e.g., Bellahcene et al., Am. J. Pathol., 146, 95-100 (1995)), and 54.2% of infiltrating ductal carcinoma of the breast. See, e.g., Kim et al., J. Korean Med. Sci., 13, 652-657 (1998). SPARC expression also has been associated with frequent microcalcification in breast cancer. See, e.g., Bellahcene et al., supra (suggesting that SPARC expression may be responsible for the affinity of breast metastases for the bone).

While SPARC possesses a number of properties, one that has been exploited is its ability to bind albumin. See, e.g., Schnitzer, J. Biol. Chem., 269, 6072 (1994). One example of the use of this property is in a FDA-approved solvent-free formulation of paclitaxel indicated in the treatment of metastatic breast cancer, Abraxane® (Abraxis BioScience, Inc., Santa Monica, Calif.). Nab-Paclitaxel utilizes the natural properties of albumin to reversibly bind paclitaxel, transport it across the endothelial cell, and concentrate it in areas of tumor. More specifically, the mechanism of drug delivery involves, in part, glycoprotein 60-mediated endothelial cell transcytosis of paclitaxel-bound albumin and accumulation in the area of tumor by albumin binding to SPARC. Clinical studies have shown that nab-paclitaxel is significantly more effective than other paclitaxel formulations, almost doubling the response rate, increasing time to disease progression and increasing survival in second-line patients. See Gradishar, Expert Opin. Pharmacother. 7(8):1041-53 (2006).

SPARC has affinity for a wide variety of ligands other than albumin, including cations (e.g., Ca2+, Cu2+, Fe2+), growth factors (e.g., platelet derived growth factor (PDGF), and vascular endothelial growth factor (VEGF)), extracellular matrix (ECM) proteins (e.g., collagen I-V and collagen IX, vitronectin, and thrombospondin-1), endothelial cells, platelets, and hydroxyapaptite. As disclosed herein, SPARC also interacts with Procaspase 8.

A cascade of protease reactions is responsible for the apoptotic changes observed in mammalian cells undergoing programmed cell death or apoptosis. This cascade involves members of the aspartate-specific cysteine proteases of the ICE/CED3 family, also known as the Caspase family. A variety of stimuli can trigger apoptosis and two major apoptotic signaling pathways, "extrinsic" and "intrinsic", converge biochemically leading to its execution (FIG. 1A). The extrinsic pathway is triggered by the activation of death receptors, such as Fas; the tumor necrosis factor-related apoptosis-inducing ligand (TRAIL) receptors, DR4 or DR5; or tumor necrosis factor receptor, which trigger death signals when bound by their natural ligands. Ligand binding to the receptor recruits adaptor proteins, such as Fas-associated death domain (FADD), which recruits Procaspase 8 to form death inducing signaling complexes (DISCs).

caspase 8 is activated at DISCs (i.e., converted from Procaspase 8 to Caspase 8 by peptide cleavage), leading to downstream pro-apoptotic events. The intrinsic pathway is centered around the mitochondria which is key in regulating the balance between pro- and anti-apoptotic factors, such as anti-apoptotic members Bcl-2, Bcl-XL and pro-apoptotic members Bax, Bak and Bok. It can be triggered by a number of stimuli., including agents that cause DNA damage or growth factor deprivation. This leads to the permeabilization of the mitochondrial membrane, the release of cytochrome c into the cytosol, which then interacts with APAF-1 to recruit Caspase 9, resulting in cleavage of executioner Caspases and apoptosis. The convergence of the extrinsic and intrinsic pathways occur when Caspase 8 activates Bid, a Bcl-2 family member that can trigger downstream targets to initiate the intrinsic apoptotic pathway.

BRIEF SUMMARY OF THE INVENTION

In one aspect, the present invention provides a composition that directs a therapeutic or diagnostic agent to a disease site in a mammal. The composition comprises a therapeutic or diagnostic agent coupled to a Procaspase 8 polypeptide and a pharmaceutically acceptable carrier. In particular, the invention provides a composition comprising a therapeutic or diagnostic agent coupled to a Procaspase 8 polypeptide with an amino acid sequence comprising one or more of SEQ ID NOS: 1-18, 25, 26 and a pharmaceutically acceptable carrier.

In another aspect, the present invention provides a method for delivering a therapeutic or diagnostic agent to a disease site in a mammal. The method comprises administering to the mammal a therapeutically or diagnostically effective amount of a pharmaceutical composition comprising the therapeutic or diagnostic agent coupled to a Procaspase 8 polypeptide and a pharmaceutically acceptable carrier.

Further, the present invention provides kits for treating or diagnosing a disease in a mammal, the kits comprising a therapeutic or diagnostic agent coupled to a Procaspase 8 polypeptide and instructions for use.

In another aspect, the invention provide pharmaceutical compositions for the treatment or diagnosis of a disease comprising a therapeutic or diagnostic agent coupled to a polypeptide comprising the sequence of SEQ ID NO: 20 or a fragment thereof and a pharmaceutically acceptable carrier, wherein the polypeptide comprising the sequence of SEQ ID NO: 20 or fragment binds to Procaspase 8.

BRIEF DESCRIPTION OF THE DRAWINGS

FIG. 5: Interaction between Procaspase 8 and SPARC is detected at the cell membrane.

FIG. 9: Interaction between Bcl-2 and Procaspase 8 occurs in the same region as where SPARC interacts with Procaspase 8.

DETAILED DESCRIPTION OF THE INVENTION

Figure 1B:
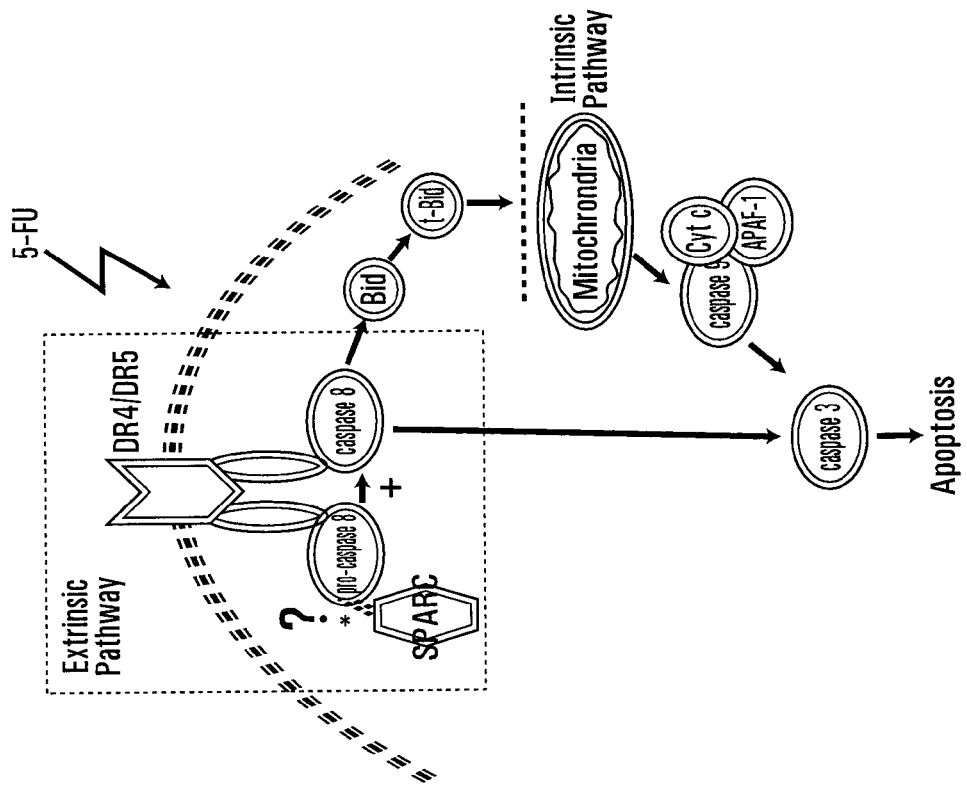
FIG. 1: Schematic of signaling events in apoptosis: A potential model of SPARC-mediated induction of apoptosis.
Figure 1A:
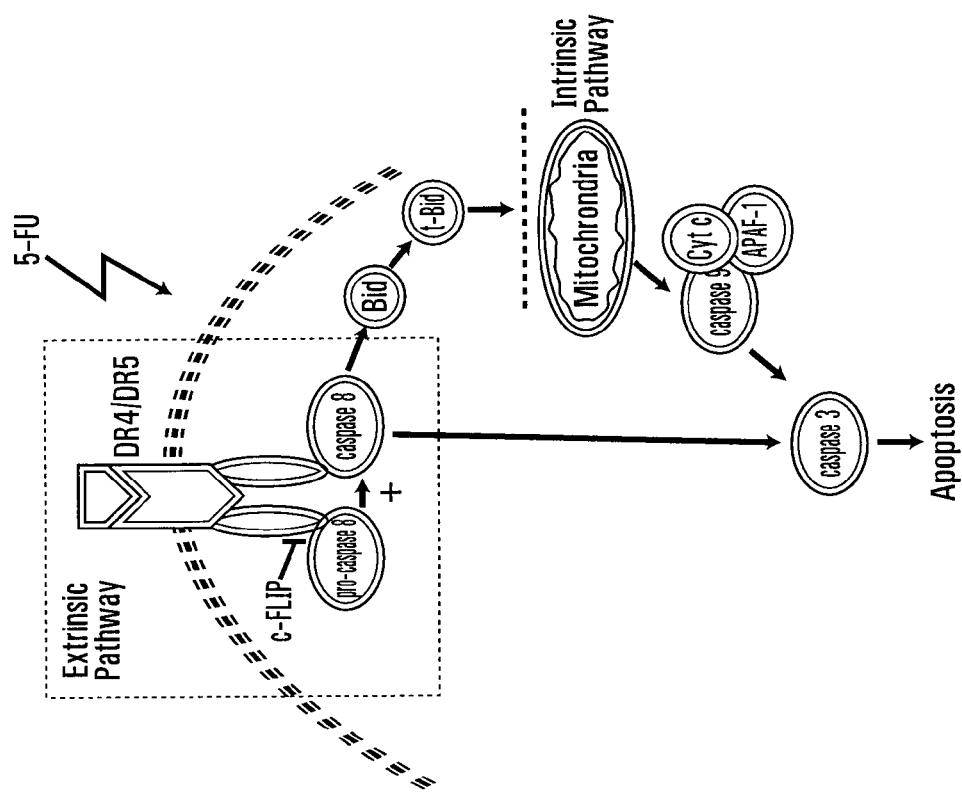

The apoptotic pathway includes the extrinsic or intrinsic pathways of apoptosis. The extrinsic pathway involves death receptors (DR4, DR5, brown), adaptor proteins (FADD), and Caspase 8 or 10, while the intrinsic pathway is centered around the mitochondria and involves Caspase 9 and cytochrome c (FIG. 1A). Without desiring to be bound by any theory, the present invention appears to be based on a novel interaction (*) between SPARC and Procaspase 8 that results in cleavage of Procaspase 8 (FIG. 1B) following exposure to chemotherapy (5-FU). This leads to the activation of the mitochondrial pathway of apoptosis via Bid, and appears to be independent of the death receptor activation. Procaspase 8 is known to exist in multiple isoform polypeptides, including mutant forms (see SEQ ID NOS: 1-18, 25, 26).

One aspect of the present invention provides a method for delivering a therapeutic or diagnostic agent to a disease site in a mammal. The method comprises administering to the mammal a therapeutically or diagnostically effective amount of a pharmaceutical composition comprising the therapeutic or diagnostic agent coupled to a Procaspase 8 polypeptide and a pharmaceutically acceptable carrier.

In another aspect, the invention provides a pharmaceutical composition for the treatment or diagnosis of a disease comprising a therapeutic or diagnostic agent coupled to a polypeptide comprising the sequence of SEQ ID NO: 20 and a pharmaceutically acceptable carrier, wherein the polypeptide comprising the sequence of SEQ ID NO: 20 binds to Procaspase 8. By "binds to Procaspase 8" it is meant, interacts specifically and with an adequate avidity to co-immunoprecipitate with a full-length, amino-terminal histidine tagged Procaspase 8 isoform.

Further, the invention provides pharmaceutical compositions for the treatment or diagnosis of a disease comprising the therapeutic or diagnostic agent coupled to a polypeptide comprising the fragments of the sequence of SEQ ID NO: 20 and a pharmaceutically acceptable carrier, wherein the fragments bind to Procaspase 8. Said fragments are made up of consecutive amino acids in the sequence SEQ ID NO: 20 of a length of at least 6 amino acids, preferably at least 9 amino acids, more preferably at least 12 amino acids, even more preferably at least 18 amino acids, and most preferably at least 36 amino acids.

Accordingly, the invention also provides a method for delivering a therapeutic or diagnostic agent to a disease site in a mammal comprising administering to the mammal a therapeutically or diagnostically effective amount of a pharmaceutical composition comprising the therapeutic or diagnostic agent coupled to a polypeptide comprising the sequence of SEQ ID NO: 20 or a fragment thereof, and a pharmaceutically acceptable carrier, wherein the polypeptide comprising the sequence of SEQ ID NO: 20 or fragment binds to Procaspase 8.

In the various aspects of the present invention described herein, the Procaspase 8 polypeptide is a polypeptide having at least 70%, desirably at least 80%, more desirably at least 90% and preferably at least 95%, sequence identity to at least 12 consecutive amino acids (and, desirably, such identity to at least 15, 20, 25, 30, 40, 50, 70, 100, 150, 200, 250, 275 or 300 consecutive amino acids) selected from any of SEQ ID NOS: 1-18, 25, and 26. Most preferably, the Procaspase 8 polypeptide has at least 70%, desirably at least 80%, more desirably at least 90% and preferably at least 95%, sequence identity to any of SEQ ID NOS: 1-4.

As used herein, "sequence identity" or "identity" in the context of the polypeptides refers to the residues in the two sequences that are the same when aligned for maximum correspondence over a specified comparison window. When percentage of sequence identity is used in reference to polypeptides, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity.

The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) J. Mol. Biol. 48:443 453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

In order to further exemplify what is meant by conservative substitution in the context of the present invention, Groups A-F are listed below. The replacement of one member of the following groups by another member of the same group is considered to be a conservative substitution.

Group A includes leucine, isoleucine, valine, methionine, phenylalanine, serine, cysteine, threonine, and modified amino acids having the following side chains: ethyl, isobutyl, —$CH_2CH_2OH$, —$CH_2CH_2CH_2OH$, —$CH_2CHOHCH_3$ and $CH_2SCH_3$.

Group B includes glycine, alanine, valine, serine, cysteine, threonine, and a modified amino acid having an ethyl side chain.

Group C includes phenylalanine, phenylglycine, tyrosine, tryptophan, cyclohexylmethyl, and modified amino residues having substituted benzyl or phenyl side chains.

Group D includes glutamic acid, aspartic acid, a substituted or unsubstituted aliphatic, aromatic or benzylic ester of glutamic or aspartic acid (e.g., methyl, ethyl, n-propyl, iso-propyl, cyclohexyl, benzyl, or substituted benzyl), glutamine, asparagine, CO—NH-alkylated glutamine or asparagine (e.g., methyl, ethyl, n-propyl, and iso-propyl), and modified amino acids having the side chain —$(CH_2)_3COOH$, an ester thereof (substituted or unsubstituted aliphatic, aromatic, or benzylic ester), an amide thereof, and a substituted or unsubstituted N-alkylated amide thereof.

Group E includes histidine, lysine, arginine, N-nitroarginine, p-cycloarginine, g-hydroxyarginine, N-amidinocitruline, 2-amino guanidinobutanoic acid, homologs of lysine, homologs of arginine, and ornithine.

Group F includes serine, threonine, cysteine, and modified amino acids having $C_1$-$C_5$ straight or branched alkyl side chains substituted with —OH or —SH.

The Procaspase 8 polypeptides, SEQ ID NO: 20 polypeptides, and fragment of SEQ ID NO: 20 contemplated by the present invention may be synthesized, detected, quantified and purified using known technologies. For example, cells expressing exogenous Procaspase 8 polypeptides can be generated by placing the Procaspase 8 structural gene/cDNA under the control of strong promoter/translation start and the vector transfected into mammalian cells to drive the expression of Procaspase 8 polypeptides in these cells. Alternatively, Procaspase 8 polypeptides may be expressed using bacculovirus or other viruses such as adenovirus. Accordingly, the invention provides for isolated recombinant polynucleotides encoding polypeptides comprising the amino acid sequences SEQ ID NOS: 1-26 and cells comprising said recombinant polynucleotides.

Suitable methods of protein detection and quantification include Western blot, enzyme-linked immunosorbent assay (ELISA), silver staining, the BCA assay (see, e.g., Smith et al., Anal. Biochem., 150, 76-85 (1985)), the Lowry protein assay (described in, e.g., Lowry et al., J. Biol. Chem., 193, 265-275 (1951)) which is a colorimetric assay based on protein-copper complexes, and the Bradford protein assay (described in, e.g., Bradford et al., Anal. Biochem., 72, 248 (1976)) which depends upon the change in absorbance in Coomassie Blue G-250 upon protein binding. Once expressed, the Procaspase 8 polypeptides may be purified by traditional purification methods such as ionic exchange, size exclusion, or C18 chromatography.

Procaspase 8 polypeptides, SEQ ID NO: 20 polypeptides, and fragment of SEQ ID NO: 20 contemplated by the invention can also be prepared by solid phase synthesis. As is generally known, polypeptides of the requisite length can be prepared using commercially available equipment and reagents following the manufacturers' instructions for blocking interfering groups, protecting the amino acid to be reacted, coupling, deprotection, and capping of unreacted residues. Suitable equipment can be obtained, for example, from Applied BioSystems, Foster City, Calif., or Biosearch Corporation in San Raphael, Calif. The use of solid phase synthetic methods is needed if nonencoded amino acids or D-forms of amino acids are used in the polypeptides. However, for polypeptides which are completely made up of amino acids that have codons, one can use recombinant techniques, e.g, use synthesized DNA sequences in commercially available expression systems.

In another aspect, the present invention provides a method for delivering a therapeutic or diagnostic agent to a disease site in a mammal. This method comprises administering to the mammal a therapeutically or diagnostically effective amount of a pharmaceutical composition comprising the therapeutic or diagnostic agent coupled to an antibody to the Procaspase 8 polypeptide and a pharmaceutically acceptable carrier.

It is desirable that the Procaspase 8 polypeptides used in the various aspects of the present invention are conjugated to polyethylene glycol (PEG). PEG conjugation can increase the circulating half-life of these polypeptides, reduce the polypeptide's immunogenicity and antigenicity, and improve their bioactivity. If used, any suitable method of PEG conjugation can be used, including but not limited to, reacting methoxy-PEG with a Procaspase 8 polypeptide protein's available amino group(s) or other reactive sites such as, e.g., histidines or cysteines. In addition, recombinant DNA approaches may be used to add amino acids with PEG-reactive groups to the Procaspase 8 polypeptides and antibodies. Further, releasable and hybrid PEG-ylation strategies may be used in accordance with the aspects of the present invention, such as the PEG-ylation of Procaspase 8 polypeptide, wherein the PEG molecules added to certain sites in the Procaspase 8 polypeptide molecule are released in vivo. Examples of PEG conjugation methods are known in the art. See, e.g., Greenwald et al., Adv. Drug Delivery Rev. 55:217-250 (2003).

The present invention further contemplates that the Procaspase 8 polypeptides may include fusion proteins. For example, and without limitation, Procaspase 8 polypeptide sequences may be fused upstream or downstream of diagnostically useful protein domains (such as hapten, GFP), active protein domains (e.g., without limitation, tTF, TNF, Smar1 derived p44 peptide, interferon, TRAIL, Smac, VHL, Procaspase, Caspase, and IL-2) or toxin (e.g., without limitation, ricin, PAP, Diphtheria toxin, Pseudomonas exotoxin)

A "fusion protein" and a "fusion polypeptide" refer to a polypeptide having at least two portions covalently linked together, where each of the portions is a polypeptide having a different property. The property may be a biological property, such as activity in vitro or in vivo. The property may also be a simple chemical or physical property, such as binding to a target molecule, catalysis of a reaction, and the like. The portions may be linked directly by a single peptide bond or through a peptide linker containing one or more amino acid residues. Generally, the portions and the linker will be in reading frame with each other.

The various aspects of the present invention also contemplate that the Procaspase 8 polypeptide is coupled to a therapeutic or a diagnostic agent. By way of illustration, the coupled moiety may be Procaspase 8 polypeptide-radioinuclide, Procaspase 8 polypeptide-drug, Procaspase 8 polypeptides-immunomodulator, Procaspase 8 polypeptides-antibody (or antibody fragment) or Procaspase 8 polypeptide-toxin conjugates.

Methods for providing this coupling, e.g., covalent bonding or conjugation, are known to those skilled in the art. For example, and without limitation, free amino groups in Procaspase 8 polypeptide proteins or SEQ ID NO: 20 or fragment of SEQ ID NO: 20, such as the epsilon-amino group of lysine, may be conjugated with reagents such as carodiimides or heterobifunctional agents. Alternatively, Procaspase 8 polypeptide or SEQ ID NO: 20 or fragment of SEQ ID NO: 20 groups can be used for conjugation. Sugar moieties bound to Procaspase 8 polypeptide glycoproteins also may be oxidized to form aldehydes groups useful in a number of coupling procedures known in the art. The conjugates formed in accordance with the invention can be stable in vivo or labile, such as enzymatically degradeable tetrapeptide linkages or acid-labile cis-aconityl or hydrazone linkages.

Numerous heterobifunctional cross-linking reagents that are used to form covalent bonds between amino groups and thiol groups and to introduce thiol groups into proteins, are known to those of skill in this art (see, e.g., Cumber et al. (1992) Bioconjugate Chem. 3:397-401; Thorpe et al. (1987) Cancer Res. 47:5924-5931; Gordon et al. (1987) Proc. Natl. Acad. Sci. 84:308-312; Walden et al. (1986) J. Mol. Cell. Immunol. 2:191-197; Carlsson et al. (1978) Biochem. J. 173: 723-737; Mahan et al. (1987) Anal. Biochem. 162:163-170; Wawryznaczak et al. (1992) Br. J. Cancer 66:361-366; Fattom et al. (1992) Infection & Immun. 60:584-589). These reagents may be used to form covalent bonds between a Procaspase 8 polypeptide and any of the active agents disclosed herein. These reagents include, but are not limited to: N-succinimidyl-3-(2-pyridyldithio)propionate (SPDP; disulfide linker); sulfosuccinimidyl 6-[3-(2-pyridyldithio)propionamido]hexanoate (sulfo-LC-SPDP); succinimidyloxycarbonyl-.alpha.-methyl benzyl thiosulfate (SMBT, hindered disulfate linker); succinimidyl 6-[3-(2-pyridyldithio)propionamido]hexanoate (LC-SPDP); sulfosuccinimidyl 4-(N-maleimidomethyl)cyclohexane-1-carboxylate (sulfo-SMCC); succinimidyl 3-(2-pyridyldithio)butyrate (SPDB; hindered disulfide bond linker); sulfosuccinimidyl 2-(7-azido-4-methylcoumarin-3-acetamide) ethyl-1,3-dithiopropionate (SAED); sulfo-succinimidyl 7-azido-4-methylcoumarin-3-acetate (SAMCA); sulfosuccinimidyl 6-[alpha-methyl-alpha-(2-pyridyldithio)toluamido]hexanoate (sulfo-LC-SMPT); 1,4-di-[3'-(2'-pyridyldithio)propionamido]butane (DPDPB); 4-succinimidyloxycarbonyl-.alpha.-methyl-.alpha.-(2-pyridylthio)-toluene (SMPT, hindered disulfate linker); sulfosuccinimidyl6[.alpha.-methyl-.alpha.-(2-pyridyldithio) toluamido]hexanoate (sulfo-LC-SMPT); m-maleimidobenzoyl-N-hydroxysuccinimide ester (MBS); m-maleimidobenzoyl-N-hydroxysulfosuccinimide ester (sulfo-MBS); N-succinimidyl(4-iodoacetyl)aminobenzoate (SIAB; thioether linker); sulfosuccinimidyl(4-iodoacetyl)amino benzoate (sulfo-SIAB); succinimidyl-4(p-maleimidophenyl)butyrate (SMPB); sulfosuccinimidyl-4-(p-maleimidophenyl)butyrate (sulfo-SMPB); azidobenzoyl hydrazide (ABH).

Other heterobifunctional cleavable coupling agents include, N-succinimidyl(4-iodoacetyl)-aminobenzoate; sulfosuccinimydil (4-iodoacetyl)-aminobenzoate; 4-succinimidyl-oxycarbonyl-a-(2-pyridyldithio)-toluene; sulfosuccinimidyl-6-[a-methyl-a-(pyridyldithiol)-toluamido]hexanoate; N-succinimidyl-3-(-2-pyridyldithio)-proprionate; succinimidyl 6[3(-(-2-pyridyldithio)-proprionamido]hexanoate; sulfosuccinimidyl 6[3(-(-2-pyridyldithio)-propionamido]hexanoate; 3-(2-pyridyldithio)-propionyl hydrazide, Ellman's reagent, dichlorotriazinic acid, S-(2-thiopyridyl)-L-cysteine. Further exemplary bifunctional linking compounds are disclosed in U.S. Pat. Nos. 5,349,066, 5,618,528, 4,569,789, 4,952,394, and 5,137,877.

The Procaspase 8 polypeptide or SEQ ID NO: 20 or fragment of SEQ ID NO: 20 is optionally linked to the active agent via one or more linkers. Flexible linkers and linkers that increase solubility of the conjugates are contemplated for use, either alone or with other linkers are also contemplated herein. The linker moiety is selected depending upon the properties desired. For example, the length of the linker moiety can be chosen to optimize the kinetics and specificity of ligand binding, including any conformational changes induced by binding of the ligand to a target receptor. The linker moiety should be long enough and flexible enough to allow the polypeptide ligand moiety and the target cell receptor to freely interact. If the linker is too short or too stiff, there may be steric hindrance between the Procaspase 8 polypeptide moiety and the cell toxin. If the linker moiety is too long, the active agent may be degraded in the process of production, or may not deliver its desired effect to the target cell effectively. In some embodiments, several linkers may be included in order to take advantage of desired properties of each linker.

Any suitable linker known to those of skill in the art can be used herein. Linkers and linkages that are suitable for chemically linked conjugates include, but are not limited to, disulfide bonds, thioether bonds, hindered disulfide bonds, and covalent bonds between free reactive groups, such as amine and thiol groups. These bonds are produced using heterobifunctional reagents to produce reactive thiol groups on one or both of the polypeptides and then reacting the thiol groups on one polypeptide with reactive thiol groups or amine groups to which reactive maleimido groups or thiol groups can be attached on the other.

Peptide linkers may also be linked by expressing DNA encoding the Procaspase 8 polypeptide or SEQ ID NO: 20 or fragment of SEQ ID NO: 20, linker and, optionally, active agent as a fusion protein. Accordingly, linkers can include, but are not limited to, peptidic linkages, amino acid and peptide linkages, typically containing between one and about 60 amino acids, preferably between about 5 and 30 amino acids, more preferably between about 10 and 20 amino acids. In addition, the Procaspase 8 polypeptide or SEQ ID NO: 20 polypeptide or fragment of SEQ ID NO: 20 provided by the invention may have between one and about 60 amino acids, preferably between about 5 and 30 amino acids, more preferably between about 10 and 20 amino acids added to its amino or carboxyl terminus.

As used herein, the term "therapeutic agent" refers to a chemical compound, a biological macromolecule, or an extract made from biological materials such as bacteria, plants, fungi, or animal (particularly mammalian) cells or tissues that are suspected of having therapeutic properties, e.g., chemotherapeutic agent or radiotherapy agent. The agent may be purified, substantially purified or partially purified.

Illustrative of the therapeutic agents which may be coupled to the Procaspase 8 polypeptide or SEQ ID NO: 20 or fragment of SEQ ID NO: 20, in the manner contemplated by the present invention include, without limitation, chemotherapeutic agents (e.g., docetaxel, paclitaxel, taxanes and platinum compounds), antifolates, antimetabolites, antimitotics, DNA damaging agents, proapoptotics, differentiation inducing agents, antiangiogenic agents, antibiotics, hormones, peptides, antibodies, tyrosine kinase inhibitors, biologically active agents, biological molecules, radionuclides, adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus), mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, anti-vascular endothelial growth factor compounds ("anti-VEGFs"), anti-epidermal growth factor receptor compounds ("anti-EGFRs"), 5-fluorouracil and derivatives, a radionuclide, a kinase inhibitor (e.g., genistein).

As used herein, the term "chemotherapeutic agent" refers to an agent with activity against cancer, neoplastic, and/or proliferative diseases. Suitable chemotherapeutic agents (which includes compounds referred to as anticancer agents) that may be used accordance with the present invention include, but are not limited to, tyrosine kinase inhibitors (genistein), biologically active agents (TNF, of tTF), radionuclides ($^{131}$I, $^{90}$Y, $^{111}$In, $^{211}$At, $^{32}$P and other known therapeutic radionuclides), adriamycin, ansamycin antibiotics, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, meplhalan, methotrexate, rapamycin (sirolimus) and derivatives, mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, antimetabolites (e.g., asparaginase), antimitotics (e.g., vinca alkaloids), DNA damaging agents (e.g., cisplatin), proapoptotics (agents which induce programmed-cell-death or apoptosis) (e.g, epipodophylotoxins), differentiation inducing agents (e.g., retinoids), antibiotics (e.g., bleomycin), hormones (e.g., tamoxifen, diethylstibestrol), antiangiogenesis agents (angiogenesis inhibitors, e.g., INF-alpha, fumagillin, angiostatin, endostatin, thalidomide, and the like), biologically active polypeptides, antibodies, lectins, and toxins.

Preferred chemotherapeutic agents include docetaxel and paclitaxel as particles comprising albumin wherein more than 50% of the chemotherapeutic agent is in nanoparticle form. Most preferably, the chemotherapeutic agent comprises particles of albumin-bound paclitaxel, e.g., Abraxane®.

The pharmaceutical compositions may also include, if desired, additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the pharmaceutical composition and physiological distress.

The term "therapeutic" as used herein refers to curing or preventing, the latter illustrated by the prevention or lessening the chance of a targeted disease (e.g., cancer or other proliferative disease) or related condition thereto afflicting a subject mammal. Curative therapy refers alleviating, in whole or in part, an existing disease or condition in a mammal.

The term "therapeutically effective amount" it is meant an amount that returns to normal, either partially or completely, physiological or biochemical parameters associated with or causative of a disease or condition. A clinician skilled in the art should be able to determine the amount of the pharmaceutical composition that will be therapeutically effective relative to a particular disease or condition. By way of example, and in accordance with a preferred embodiment wherein the therapeutic agent is paclitaxel, the paclitaxel dose administered may range from about 30 mg/m$^2$ to about 1000 mg/m$^2$ with a dosing cycle of about 3 weeks (i.e., administration of the paclitaxel dose once every about three weeks), desirably from about 50 mg/m$^2$ to about 800 mg/m$^2$, preferably from about 80 mg/m$^2$ to about 700 mg/m$^2$, and most preferably from about 250 mg/m$^2$ to about 300 mg/m$^2$ with a dosing cycle of about 3 weeks.

The invention provides embodiments wherein the Procaspase 8 polypeptide or SEQ ID NO: 20 or fragment of SEQ ID NO: 20, is fused or coupled to an antibody or antibody fragment which mediates one or more of complement activation, cell mediated cytotoxicity, and opsinization. The term "antibody" herein includes, without limitation, monoclonal antibodies, polyclonal antibodies, dimers, multimers, multispecific antibodies (e.g., bispecific antibodies). Antibodies may be murine, human, humanized, chimeric, or derived from other species. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any class (e.g., IgG, IgE, IgM, IgD, and IgA) or subclass (e.g., IgG1, IgG2, IgG3, IgG4, IgA1 and IgA2) of immunoglobulin molecule. The immunoglobulins can be derived from any species.

"Antibody fragments" comprise a portion of a full length antibody, which maintain the desired biological activity.

"Antibody fragments" are generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567). Chimeric antibodies of interest herein include "primatized" antibodies comprising variable domain antigen-binding sequences derived from a non-human primate (e.g., Old World Monkey or Ape) and human constant region sequences.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express Fc.gamma.RIII only, whereas monocytes express Fc.gamma.RI, FcγRII and FcγRIII. To assess ADCC activity of a molecule of interest, an in vitro ADCC assay may be performed (U.S. Pat. Nos. 55,003,621; 5,821,337). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al PNAS (USA), 95:652-656 (1998).

An antibody which "induces cell death" is one which causes a viable cell to become nonviable. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue or 7AAD can be assessed relative to untreated cells. Cell death-inducing antibodies are those which induce PI uptake in the PI uptake assay in BT474 cells.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies).

Turning to the diagnostic aspect of the present invention, the diagnostic agents that may be used include, without limitation, radioactive agents, MRI contrast agents, X-ray contrast agents, ultrasound contrast agents, and PET contrast agents. The coupling of these agents, described in connection with therapeutic agents, is also contemplated by this aspect of the invention. Further, the term "diagnostically effective amount" is an amount of the pharmaceutical composition that in relevant clinical settings allows for a reasonably accurate determination of the presence of abnormal proliferative, hyperplastic, remodeling, inflammatory activity in tissues and organs. For example, the condition "diagnosed" in accordance with the invention can be a benign or malignant tumor.

For use in vivo, the chemotherapeutic agent coupled Procaspase 8 polypeptide or SEQ ID NO: 20 or fragment of SEQ ID NO: 20, is desirably formulated into a pharmaceutical composition comprising a physiologically acceptable carrier. Any suitable physiologically acceptable carrier can be used within the context of the invention, depending on the route of administration. Those skilled in the art will appreciate those carriers that may be used in to provide a pharmaceutical composition suitable for the desired method of administration.

The administration of the pharmaceutical compositions of the present invention may be accomplished via any suitable route including, but not limited to, intravenous, intraperitoneal, intratumoral, and inhalational administration, with intravenous and intratumoral administration being most preferred.

In the case of inhalational therapy, the pharmaceutical composition of the present invention is desirably in the form of an aerosol. Aerosol and spray generators for administering the agent if in solid form are available. These generators provide particles that are respirable or inhalable, and generate a volume of aerosol containing a predetermined metered dose of a medicament at a rate suitable for human administration. Examples of such aerosol and spray generators include metered dose inhalers and insufflators known in the art. If in liquid form, the pharmaceutical compositions of the invention may be aerosolized by any suitable device.

When used in connection with intravenous, intraperitoneal or intratumoral administration, the pharmaceutical composition of the invention may comprise sterile aqueous and non-aqueous injection solutions, suspensions or emulsions of the active compound, which preparations are preferably isotonic with the blood of the intended recipient. These preparations may contain one or more of anti-oxidants, buffers, surfactants, cosolvents, bacteriostats, solutes which render the compositions isotonic with the blood of the intended recipient, and other formulation components known in the art. Aqueous and non-aqueous sterile suspensions may include suspending agents and thickening agents. The compositions may be presented in unit-dose or multi-dose containers, for example sealed ampoules and vials.

The methods of the present invention may also be part of combination therapy. The phrase "combination therapy" refers to administering a therapeutic agent in accordance with the invention together with another therapeutic composition in a sequential or concurrent manner such that the beneficial effects of this combination are realized in the mammal undergoing therapy.

The methods of the invention are suitable for use in diagnosing or treating various diseases including, but not limited to, abnormal conditions of proliferation, tissue remodeling, hyperplasia, exaggerated wound healing in any bodily tissue including soft tissue, connective tissue, bone, solid organs, blood vessel and the like. More specific examples of such diseases include cancer, diabetic or other retinopathy, inflammation, fibrosis, arthritis, restenosis in blood vessels or artificial blood vessel grafts or intravascular devices and the like.

In a preferred aspect, the invention provides methods of diagnosing and/or treating a tumor, wherein the tumor is selected from the group consisting of oral cavity tumors, pharyngeal tumors, digestive system tumors, the respiratory system tumors, bone tumors, cartilaginous tumors, bone metastases, sarcomas, skin tumors, melanoma, breast tumors, the genital system tumors, urinary tract tumors, orbital tumors, brain and central nervous system tumors, gliomas, endocrine system tumors, thyroid tumors, esophageal tumors, gastric tumors, small intestinal tumors, colonic tumors, rectal tumors, anal tumors, liver tumors, gall bladder tumors, pancreatic tumors, laryngeal tumors, tumors of the lung, bronchial tumors, non-small cell lung carcinoma, small cell lung carcinoma, uterine cervical tumors, uterine corpus tumors, ovarian tumors, vulvar tumors, vaginal tumors, prostate tumors, prostatic carcinoma, testicular tumors, tumors of the penis, urinary bladder tumors, tumors of the kidney, tumors of the renal pelvis, tumors of the ureter, head and neck tumors, parathyroid cancer, Hodgkin's disease, Non-Hodgkin's lymphoma, multiple myeloma, leukemia, acute lymphocytic leukemia, chronic lymphocytic leukemia, acute myeloid leukemia, chronic myeloid leukemia. In addition, the invention provides for method of predicting or determining a tumor's response to a chemotherapeutic agent, methods of treating a tumor, and kits for predicting the response of a mammalian tumor to a chemotherapeutic agent, wherein the tumor is a sarcoma, adenocarcinoma, squamous cell carcinoma, large cell carcinoma, small cell carcinoma, basal cell carcinoma, clear cell carcinoma, oncytoma or combinations thereof.

Further, and in a related aspect, the invention provides a method of predicting or determining a tumor's response to a chemotherapeutic agent, as well as a method of predicting or determining a proliferative disease's response to a chemotherapeutic agent or treating a proliferative disease, including but, not limited to, where the proliferative diseases is, e.g., benign prostatic hyperplasia, endometriosis, endometrial hyperplasia, atherosclerosis, psoriasis or a proliferative renal glomerulopathy.

The invention provides for embodiments wherein the disease is in a mammal, including but not limited to, a human.

The following examples further illustrate the invention but should not be construed as in any way limiting its scope.

EXAMPLE 1

This example demonstrates the specific binding of anti-SPARC antibody to SPARC.

Whole cell extract was prepared from HUVEC cells by sonication. The protein was separated on a 5-15% SDS-PAGE, transferred onto PVDF membrane and visualized with a polyclonal antibody against SPARC and a monoclonal antibody against SPARC. Both antibodies reacted to a single band at 38 kDa, the correct molecular weight for SPARC. When MX-1 tumor cell line was analyzed by the same method, SPARC was detected in both the clarified cell lysate or the membrane rich membrane fraction.

EXAMPLE 2

This example demonstrates the absence of SPARC expression in normal tissues.

Normal human and mouse tissue were immunostained and scored (0-4) for SPARC staining using a tumor and normal tissue array. Immunostaining was performed using polyclonal rabbit anti-SPARC antibody. SPARC was not expressed in any of the normal tissues, with the exception of the esophagus. Likewise, SPARC was not expressed in any of the normal mouse tissue, except the kidney of the female mouse. However, it is possible that this expression was due to follistatin which is homologous to SPARC.

| SPARC Expression in Human Normal Tissues | |
|---|---|
| Stomach | 0/8 |
| Colon | 0/9 |
| Rectum | 0/15 |
| Liver | 0/14 |
| Spleen | 0/10 |
| Lung | 0/14 |
| Kidney | 1/14 |
| Brain | 1/14 |
| Testis | 0/8 |
| Prostate | 0/3 |
| Heart | 0/9 |
| Tonsil | 0/10 |
| Lymph Nodes | 0/10 |
| Appendix | 0/10 |
| Esophagus | 5/5 |
| Pancreas | 0/5 |
| Eyeball | 0/5 |
| Ovary | 0/5 |

| Mouse Normal Tissues | |
|---|---|
| Liver | 0/19 |
| Kidney (M) | 0/8 |
| Kidney (F) | 6/8 |
| Lung | 0/16 |
| Muscle | 0/20 |
| Brain | 0/20 |
| Heart | 0/18 |
| Stomach | 0/20 |
| Spleen | 0/20 |

EXAMPLE 3

This example illustrates the expression of SPARC in MX-1 tumor cells.

MX-1 cells were cultured on a coverslip and stained with an antibody directed against human SPARC using methods known in the art. Antibody staining was observed, which demonstrates that MX-1 is expressing SPARC. These results suggest that SPARC expression detected in MX-1 tumor cells is a result of SPARC secretion by MX-1 tumor cells. Staining was more intense for MX-1 tumor cells than that of normal primary cells such as HUVEC (human umbiblical vein endothelial cells), HLMVEC (Human lung microvessel endothelial cells), and HMEC (Human mammary epithelial cells). Though the majority of the SPARC staining was internal SPARC, significant level of surface SPARC was detected as demonstrated by confocal miscroscopy and staining of unpermeabilized cells.

EXAMPLE 4

This example illustrates the overexpression of SPARC protein in human breast carcinoma cells.

SPARC expression in human breast carcinoma cells was determined using a tumor array from Cybrdi, Inc. (Gaithersburg, Md.). The results of this analysis are set forth in Table 1. Intensity of staining was scored from "Negative" to 4+, with the higher number corresponding to greater intensity of overexpression. 49% of breast carcinoma stained positive (2+ and above) for SPARC, as compared to 1% of normal tissue (p<0.0001).

| | SPARC Staining (%) | | | | | |
|---|---|---|---|---|---|---|
| | Negative | –/+ | 1+ | 2+ | 3+ | 4+ |
| Carcinoma Cells | 31 (34%) | 14 (15%) | 1 (1%) | 11 (12%) | 9 (10%) | 25 (27%) |
| Normal Cells | 93 (89%) | 7 (7%) | 4 (4%) | 1 (1%) | 0 (0%) | 0 (0%) |

EXAMPLE 5

This example demonstrates SPARC overexpression in squamous cell head and neck cancers with high response rates using nanoparticle albumin-bound paclitaxel (ABI-007).

In phase I and II clinical studies of patients with squamous cell carcinoma (SCC) of head and neck (H&N) and anal canal, response rates of 78% and 64% were observed, respectively, for intra-arterially delivered Nanoparticle Albumin-Bound Paclitaxel (Abraxane®, ABX or ABI-007) (see, e.g., Damascelli et al., Cancer, 92(10), 2592-2602 (2001), and Damascelli et al., AJR, 181, 253-260 (2003)). In comparing in vitro cytotoxicity of ABX and Taxol (TAX), we observed that a squamous cervix (A431) line demonstrated improved $IC_{50}$s for ABX (0.004 µg/ml) vs TAX (0.012 µg/ml). Albumin-mediated transendothelial caveolar transport of paclitaxel (P) and increased intratumoral accumulation of P for ABX vs TAX was demonstrated recently (see, e.g., Desai, SABCS 2003).

Human H&N tumor tissues (n=119) and normal human H&N tissue (n=15) were immunostained and scored (0-4+) for SPARC staining using a tumor and normal tissue array. Immunostaining was performed using polyclonal rabbit anti-SPARC antibody. In a new phase I dose escalation study (ABX given IV over 30 minutes q3w), a subset of head and neck cancer patients (n=3) were analyzed for response to ABX.

SPARC was overexpressed (score>2+) in 60% (72/119) of the H&N tumors versus 0% (0/15) in normal tissues (p<0.0001).

| | SPARC Staining (%) | | | | | |
|---|---|---|---|---|---|---|
| | Negative | –/+ | 1+ | 2+ | 3+ | 4+ |
| H&N Tumor Array: Carcinoma Cells | 17 (14%) | 14 (12%) | 16 (13%) | 23 (19%) | 20 (17%) | 29 (24%) |
| Normal Cells | 13 (87%) | 0 (0%) | 2 (13%) | 0 (0%) | 0 (0%) | 0 (0%) |

In a new phase I dose escalation study (ABX given IV over 30 minutes q3w), a subset of head and neck cancer patients (n=3) were analyzed for response to ABX. In this study, ⅔ H&N patients achieved partial response (PR) after 2 cycles of treatment at dose levels of 135 mg/m² (1 pt) and 225 mg/m² (1 pt). A third patient at 260 mg/m² progressed. Tumor tissues from these patients were stained for SPARC and 1 of the responding patients showed strong overexpression for SPARC.

EXAMPLE 6

1. Materials and Methods

Cell Lines: MIP101 and HCT116 (ATCC) human CRC cells were maintained in DMEM media supplemented with 1% penicillin-streptomycin, 1% kanamycin (Invitrogen) and 10% newborn calf serum at 37° C. and 5% $CO_2$. For MIP101 cells resistant to 5-FU (MIP/5FU) or CPT-11 (MIP/CPT), media were also supplemented with 500 µM 5-FU or 10 µM CPT-11, respectively. MIP101 transfected with empty vector (VIIP/ZEO) and MIP101 cells stably transfected with SPARC (MIP/SP), were also supplemented with 0.01% zeocin (Invitrogen).

RT-PCR: Cells were seeded at 150,000 cells/well in 6-well plates. After 24 hours, cells were incubated with 1000 µM 5-FU for 0-4 hours and RNA isolated 24 hours later with Trizol (Invitrogen) [12]. 1 µg of total RNA was used to generate cDNA (Superscript III, Invitrogen). Specific primers were used as previously described for SPARC [12]; others include:

```
caspase 8: 5'-ATCACAGACTTTGGACAAAGTTTA-3' (sense),
5'-TCTGAATCAGTCTCAACAGGTATA-3' (anti-sense);

caspase 10: 5'-AAGCTTCTGATTATTGATTCAAACC-3'
(sense),
5'-TTCTCTATGTTTCTCAAAAGTTTA-3' (anti-sense);

DR4: 5'-GGACAATGCTCACAACGAGA-3' (sense),
5'-TGTTGACCCATTTCATCAGC-3' (anti-sense);

FADD: 5'-TGTGCAGCATTTAACGTCATATGT-3' (sense),
5'-ACGCAGCTTGAGTTCAGAA-3' (antisense);

TRADD: 5'-TTTGAGTTGCATCCTAGCCCA-3' (sense),
5'-GCTGGTGAGCTCGTTCTC-3' (anti-sense);
and -continued
β-actin: 5'-GCCACGGCTGCTTCCAG-3' (sense),
5'-GGCGTACAGGTCTTT C-3' (anti-sense).
```

PCR settings: 94° C. for 3-5 minutes, followed by 32-41 cycles at: 94° C. for 20-60 seconds; followed by: (SPARC): 65° C. for 1 minute, (caspase 8, DR4 and (β-actin): 58° C. for 15 seconds, (caspase 10 and TRADD): 50° C. for 15 seconds, (FADD): 55° C. for 15 seconds; then 72° C. for 30-60 seconds; followed by extension at 72° C. for 7-10 minutes. PCR products were separated on a 1.5% agarose gel electrophoresis, imaged used for quantitation of expression levels, and values normalized to β-actin levels.

Immunoblot Analysis: 48 hours after seeding, cells were incubated with 1000 µM 5FU, and collected at 0-12 hours for protein. 40 µg total protein/sample was loaded, separated on a 12% SDS-PAGE, then transferred to PDVF membranes (Bio-Rad). Immunodetection was performed using antibodies against Caspase 8, FADD, p-FADD, Caspase 10, BID, Caspase 9, and Caspase 3 (all 1:1000, Cell Signaling Technologies); and cleaved Caspase 8 (1:1000, Calbiochem), followed by incubation with the appropriate secondary antibody. All immunoblots were also probed with antibodies to β-actin (0.32 μg/mL, Abcam) as loading control. Proteins were detected with SuperSignal West Dura (Pierce).

RNA Interference: Initially, to assess the efficiency of Caspase 8 gene expression knock-down by siRNA, MIP/SP and HCT116 cells were seeded (6-well plate). 24 hours later, cells were transiently transfected with 20-60 nM scramble oligonucleotide sequence (control), or Caspase 8 siRNA (Stealth RNAi, Invitrogen) and cells collected at various time intervals following transfection. 40 nM of siRNA yielded the most efficient knock-down (14-fold decrease in Caspase 8 expression at 48-96 hours). For all subsequent experiments, 40 nM of siRNA or scramble control was used. Following Caspase 8 siRNA transfection, cells were assessed for cell viability, and apoptosis using either Caspase 3/7 assay or TUNEL assay.

Cell Viability Assay: 24 hours after seeding (~60% confluence), cells were transiently transfected with Caspase 8 siRNA for 48 hours before incubation with 1000 μM 5-FU or 100 μM CPT-11 for 48 hours. Cell viability was assessed by MTS assay (Promega) at 490 nm. Caspase 3/7 Assay: Cells were transiently transfected with 40 nM of Caspase 8 siRNA for 48 hours, and incubated with 1000 μM 5-FU for another 48 hours. Total cell lysates were isolated and 20 μg of total protein/sample were used in Caspase-Glo 3/7 Assay (Promega), using a 1:1 dilution of Caspase-Glo 3/7 Substrate. Relative luminescence units (RLU) was quantified using a Viktor2 1420 Multilabel counter (Perkin Elmer).

TUNEL Assay: Cells were seeded (24-well plates) to achieve ~60% confluence 24 hours later for transient transfection with Caspase 8 siRNA. 36 hours later, cells were incubated with 1000 μM 5-FU for 36 hours, harvested (suspension and attached cells) and fixed onto glass slides with Shandon cytospin at 2000 rpm for 10 minutes and stained as per manufacturer's instructions (Promega). The number of TUNEL-positive cells was counted and averaged from four different fields (n=4 independent experiments, with slides read independently by two individuals in a blinded fashion).

caspase 8/9 Inhibition: Cells were seeded (96-well plates), and incubated 24 hours later (~60% confluence) with 10-50 μM of Caspase 8-like inhibitor (z-IETD-fmk, Sigma) or Caspase 9-like inhibitor (z-LEHDfmk•TFA, Sigma) for 30 minutes, followed by incubation with 1000 μM 5-FU for an additional 24 hours. Cell viability was assessed by MTS assay.

Subcellular Fractionation and Immunoprecipitation: MIP/SP and HCT116 cells were grown until ~80% confluence, incubated with 1000 μM 5-FU and isolated at 0-4 hours. Cells were separated into nuclear, cytosolic, and membrane fractions using ProteoExtract Subcellular Proteome Extraction Kit (EMD Biosciences Inc.). 250 μg of the individual cellular fractions were incubated with α-SPARC (10 μg/mL, Haematologic Technologies), α-caspase 8 (1:100) or a non-specific anti-mouse IgG antibody as control (Cell Signaling Technologies), in PBS overnight (4° C.) with gentle agitation. Protein:Antibody mixture was then incubated with 30 μL of Protein A: Protein G (Sigma) (1:1) beads for 4 hours (4° C.). Proteins were also incubated with EZView Red His-Select HC Nickel affinity gel (Sigma) for immunoprecipitation of His-tagged SPARC protein. For all complexes, beads were washed 5× with PBS, eluted with 40 μL of 2×SDS-Loading Buffer, and used for immunoblotting against SPARC, Caspase 8, p-FADD, and DR4 (0.5 μg/mL, Santa Cruz).

Animal Studies: Tumors harvested from xenografts from animals (NIH nude mice, 6 weeks old, Taconic Laboratories) were used for histology, RT-PCR or immunoblot. 2×10$^6$ MIP101 cells were injected into the left flank. Once tumors reached 100 mm$^3$, animals were treated with chemotherapy using 3-week cycle regimen (×2 cycles) as previously described (Tai I T, Dai M, Owen D A, Chen L B: Genome-wide expression analysis of therapy-resistant tumors reveals SPARC as a novel target for cancer therapy. J Clin Invest 2005; 115: 1492-502.)

Experimental groups (2 animals/group) for this study included treatment with: SPARC, SPARC+5-FU, 5-FU only, and saline. In addition, tumor xenografts of MIP/ZEO and MIP/SP cells from nude mice treated with either 5-FU (three consecutive days) or saline, were collected after the 1st cycle of treatment and homogenized (Kinematica, POLYTRON-Aggregate). Lysates were then prepared for immunoblot or RT-PCR. All animals received care according to standard animal care protocol and guidelines. For histology, tissue sections of tumor xenografts were processed for immunohistochemistry based on previously established protocols (Tai I T, Dai M, Owen D A, Chen L B: Genome-wide expression analysis of therapy-resistant tumors reveals SPARC as a novel target for cancer therapy. J Clin Invest 2005; 115:1492-502.). Similarly, cells seeded on coverslips at 150,000 cells/well in a E-well plate, treated 24 hours later with 1000 μM 5-FU for 2 hours were then fixed in 2% paraformaldehyde and processed for immunofluorescence staining as previously described [27]. In both cases, α-caspase 8 (1:50, paraffin-embedded tissues; 1:100, cells on coverslips) antibody was used and incubated overnight at 4° C., and counterstained with DAPI. Zeiss Axioplan 2 Fluorescence microscope was used for image capture.

Statistics: Statistical difference between experimental groups were calculated and analyzed using Student's t-test. Statistical significance was defined as $p<0.05$, using Smith's Statistical Package.

2. Results

SPARC-over expressing MIP 101 cells have higher levels of expression of genes involved in the extrinsic pathway of apoptosis.

Figures 2A, 2B:
FIG. 2: The presence of higher levels of SPARC is associated with greater expression of genes involved in the extrinsic pathway of apoptosis following exposure to 5-FU.
Figure 2C:
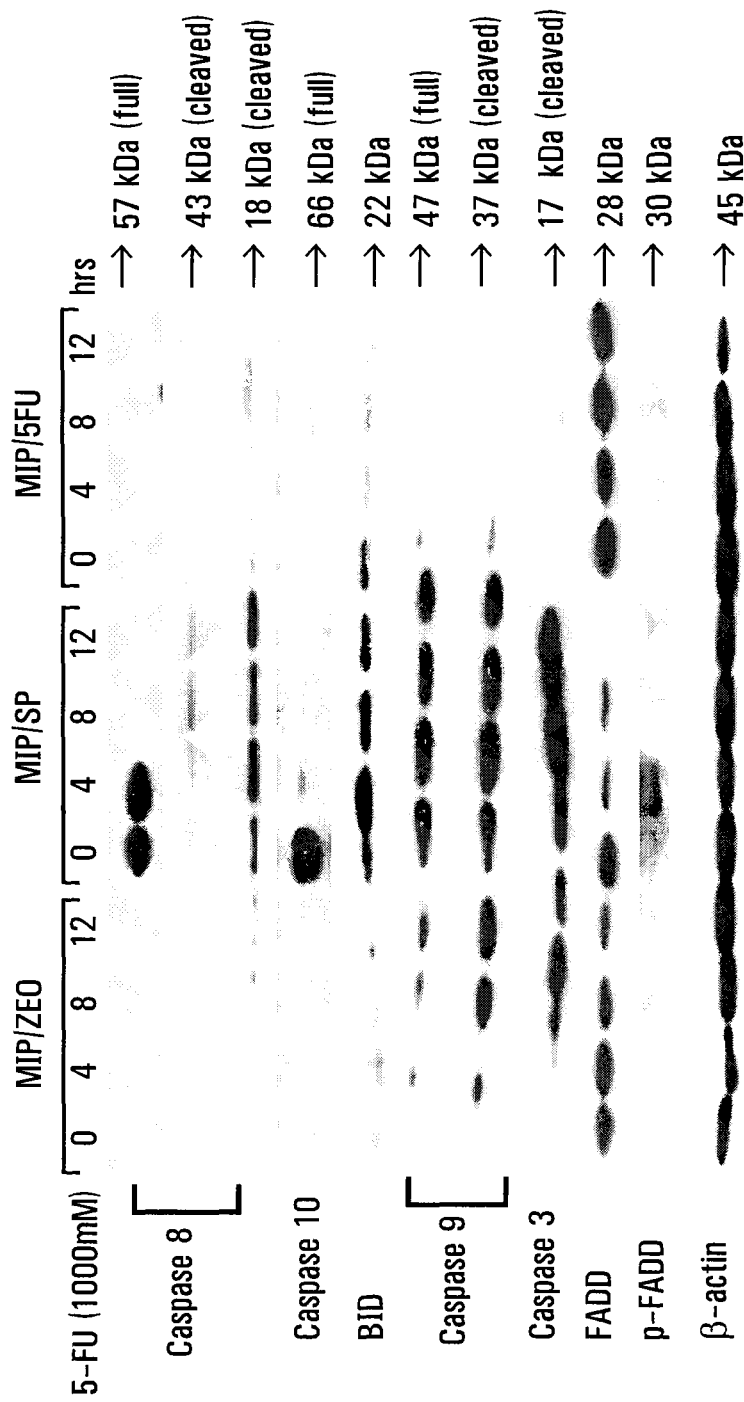
Figure 2D:
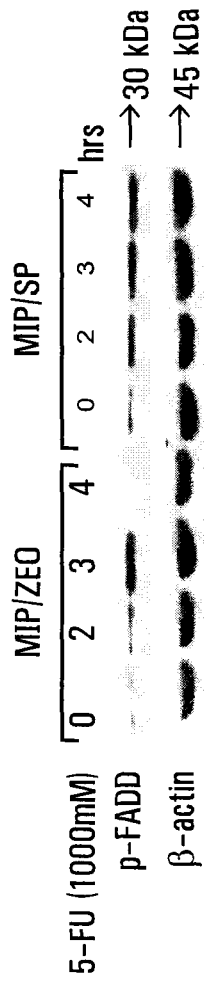
Figure 2E:
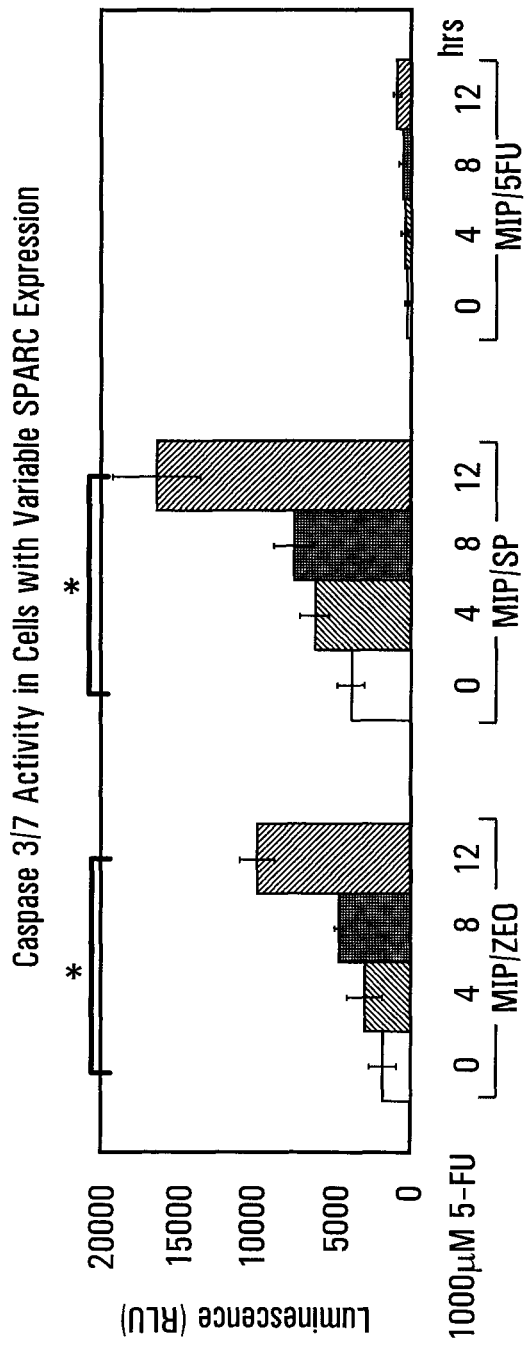

Over-expression of SPARC in MIP 101 CRC cells (MIP/SP) leads to increased sensitivity to 5-FU and CPT-11 chemotherapy by diminishing cell survival and enhancing apoptosis. In order to understand the mechanisms involved in this SPARC-mediated effect, studies began by examining the relative contribution of genes involved in apoptosis at the transcriptional level. Total RNA isolated from MIP/SP and empty-vector control cells (MIP/ZEO) were used to determine the expression levels of those involved in the extrinsic pathway of apoptosis, such as Caspase 8, Caspase 10, DR4, and FADD. It was noted that Caspase 8, 10 and FADD appeared significantly higher in MIP/SP cells, while DR4 expression was greater in control MIP/ZEO cells (FIG. 2A). The greatest difference in gene expression was observed with Caspase 8 and 10, which were 6.7 and 4.8-fold higher in MIP/SP than MIP/ZEO respectively, thereby suggesting that differential expression of SPARC positively influenced genes involved in the extrinsic pathway of apoptosis. SPARC over-expression leads to greater activation of the extrinsic pathway of apoptosis The results noted above show a correlation between SPARC and Caspase 8 and 10 levels in MIP101 cells. This prompted an assessment of whether the extrinsic pathway may be involved in SPARC-mediated apoptosis. It had been observed a greater number of cells undergoing apoptosis when either sensitive MIP 101 or 5-FU resistant MIP 101 cells (MIP/5FU) were exposed to SPARC in combination with 5-FU in vitro and in vivo. Based on these findings, the effect of 5-FU exposure on the extrinsic pathway in cells with variable levels of SPARC was studied (highest in MIP/SP, moderate in MIP/ZEO and lowest in MIP/5FU). Higher levels of Caspase 8 and 10 gene expression were observed in MIP/SP cells and this increased following exposure to 5-FU 1000 µM. In cells with low SPARC expression, Caspase 8 and 10 were not observed either basally or following exposure to 5-FU in both MIP/ZEO or MIP/5FU cells (FIG. 2B). FADD gene expression increased in all cells following treatment with 5-FU, while no significant change was noted with DR4 expression with exposure to 5-FU in MIP/SP or MIP/5FU while a decrease was noted in MIP/ZEO. This heightened basal expression of Caspase 8 and 10 at the transcriptional level in cells over-expressing SPARC translated to the protein level, where MIP/SP cells again showed an abundance of pro-caspase 8 and 10, in comparison to MIP/ZEO and MIP/5FU cells prior to exposure to 5-FU (FIG. 2C). Conversion from the 57 kDa pro-caspase 8 to a cleaved product of 48 kDa occurred following treatment with 100004 of 5-FU. There were also higher basal levels of Bid in MIP/SP cells, which peaked at 4 hours after treatment with 5-FU followed by a gradual decline over the next 8 hours. Interestingly, following 5-FU treatment, activation of Caspases 9 and 3 was prominently observed in MIP/SP cells and to a lesser degree in MIP/ZEO, and even less in MIP/5FU cells. FADD was basally expressed in all cell lines, however, significantly greater phosphorylated FADD was seen in MIP/SP as early as 4 hours after treatment with 5FU in comparison to either MIP/ZEO or MIP/5FU cells (FIG. 2C). This observation that MIP/SP cells were more likely to undergo apoptosis following incubation with 5-FU than MIP/ZEO cells was further supported by significantly higher levels of Caspase 3/7 activity in MIP/SP cells at 12 hours after incubation with 5-FU than in MIP/ZEO cells (16397.0±2787.6 vs. 9954.0±1104.8, p=0.0003) (FIG. 2D).

Figure 3A:
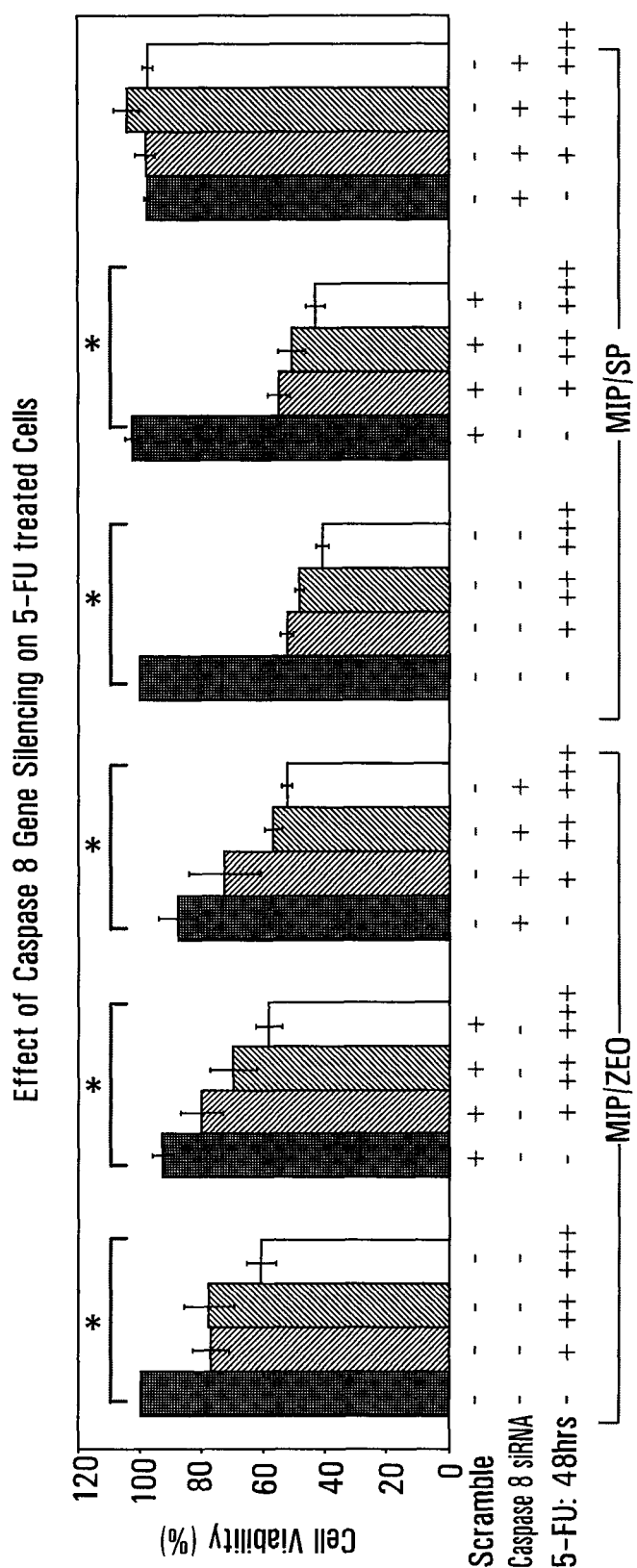
FIG. 3: Inhibition of Caspase 8 Increases Cell Viability in CRC cells with greater SPARC expression.
Figure 3B:
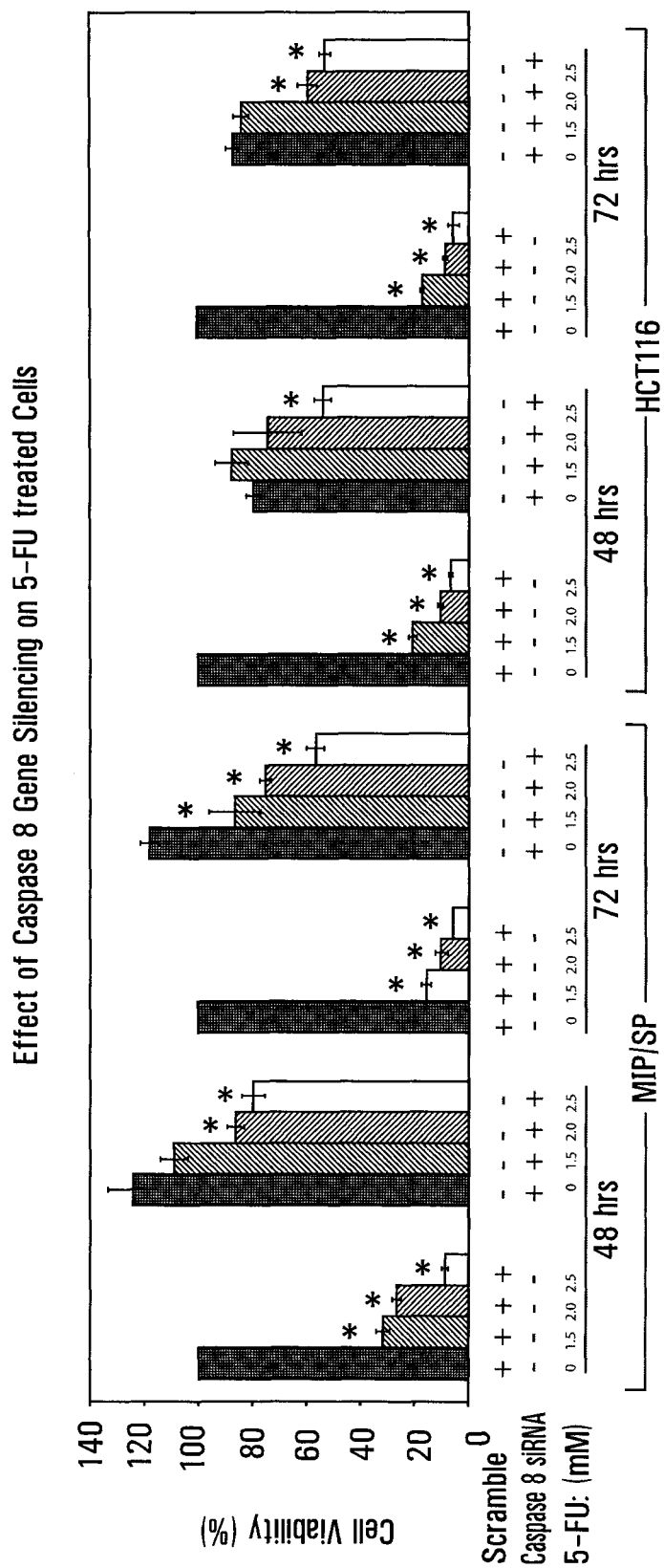
Figure 3C:
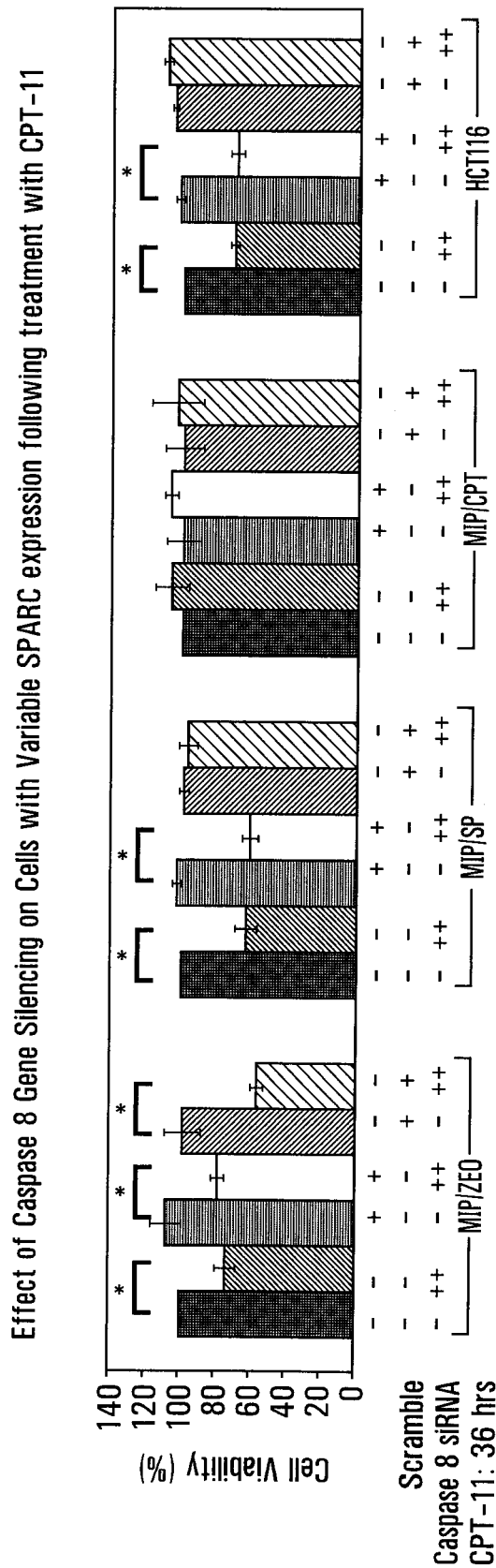

In the presence of SPARC, inhibition of Caspase 8 prevents apoptosis in response to 5-FU exposure. The relative contribution of the extrinsic pathway in SPARC-mediated apoptosis was examined by assessing the effect of reducing the transcriptional expression of Caspase 8 by siRNA. Effective knock-down of Caspase 8 was achieved by transiently transfecting MIP/SP or HCT116 cells with 40 nM Caspase 8 siRNA or a scramble oligonucleotide sequence as control. MIP/ZEO and MIP/SP cells were transiently transfected with Caspase 8 siRNA and cell viability was assessed following incremental concentrations of 5-FU (0-1200 µM). It was noted that knocking-down Caspase 8 gene expression in MIP/ZEO cells did not affect their response to 5-FU 1200 µM, as cell viability similarly decreased from 87.8±5.8 to 52.1±1.7% (p=0.0002) in comparison to control cells (FIG. 3A). However, Caspase 8 gene silencing in MIP/SP abolished the effect of 5-FU by preventing a decrease in cell viability after treatment with various concentrations of 5-FU (0-1200 µM), in comparison to cells transfected with control scramble siRNA (97.2±1.5% viable untreated cells vs 97.6±1.4% after 5-FU treatment, p=0.8783) (FIG. 3A). In order to further assess whether the effect of Caspase 8 gene silencing was dependent on SPARC expression, several CRC cell lines expressing variable levels of SPARC were examined, such as intrinsically high SPARC-expressing HCT116 cells and high SPARC-expressing MIP/SP cells; and compared them to low SPARC expressing MIP/ZEO and even lower, MIP/5FU and MIP/CPT cells. Caspase 8 gene knockdown again lessened the effect of 5-FU on MIP/SP cells, with cell viability in response to 5-FU treatment increasing by 20.3±4.0% in comparison to cells not transfected with Caspase 8 siRNA (p=0.0167) (FIG. 3B). There was no significant effect of Caspase 8 gene knock-down in MIP/ZEO cells as cell viability decreased following 5-FU treatment despite inhibition of Caspase 8 (99.3±1.5% vs. 75.5±0.5%, p=0.0004). Similarly, no effect was seen with Caspase 8 knock-down in MIP/5FU cells, as they remained unaffected by 5-FU treatment (FIG. 3B). Using a different chemotherapy, CPT-11, MIP/SP cells had a reduction in cell viability after treatment with CPT-11 100 µM (100.0±0.0001% vs. 63.4±4.9%, p=0.00003), which was again abolished after transfection with Caspase 8 siRNA despite the presence of CPT-11 (98.4±3.1% vs. 97.2±4.0%, p=0.8092) (FIG. 3C). The most interesting finding was that a similar effect of Caspase 8 gene silencing was observed with high SPARC-expressing HCT116 cells, as with MIP/SP cells, with decreased sensitivity to either 5-FU or CPT-11 in comparison to untreated cells (FIGS. 3B and C). For example, 88.2±2.3% viable cells in the presence of Caspase 8 siRNA+5-FU vs. 87.5±5.4% in untreated controls (p=0.88).

Figure 3D:
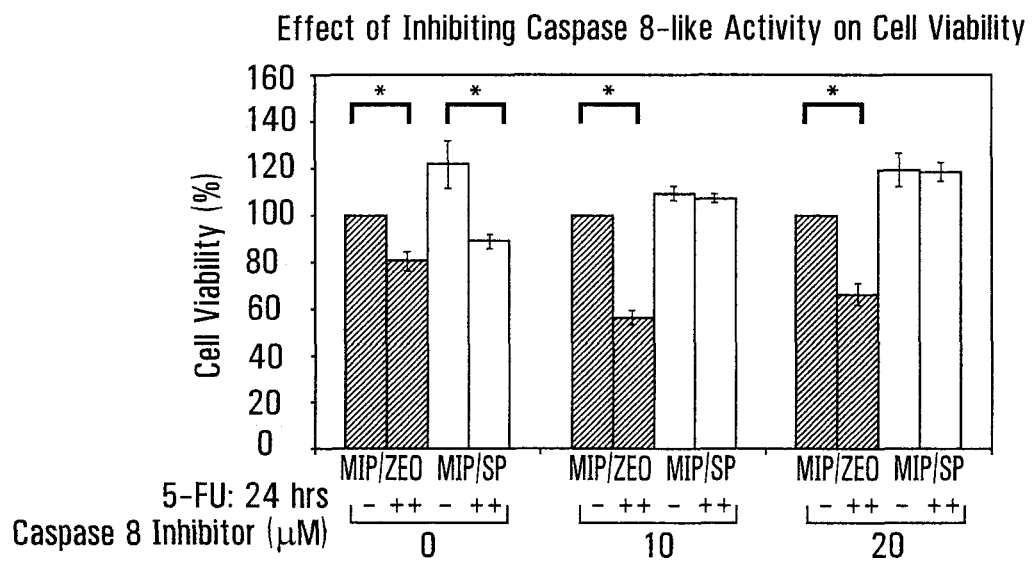
Figure 3D:
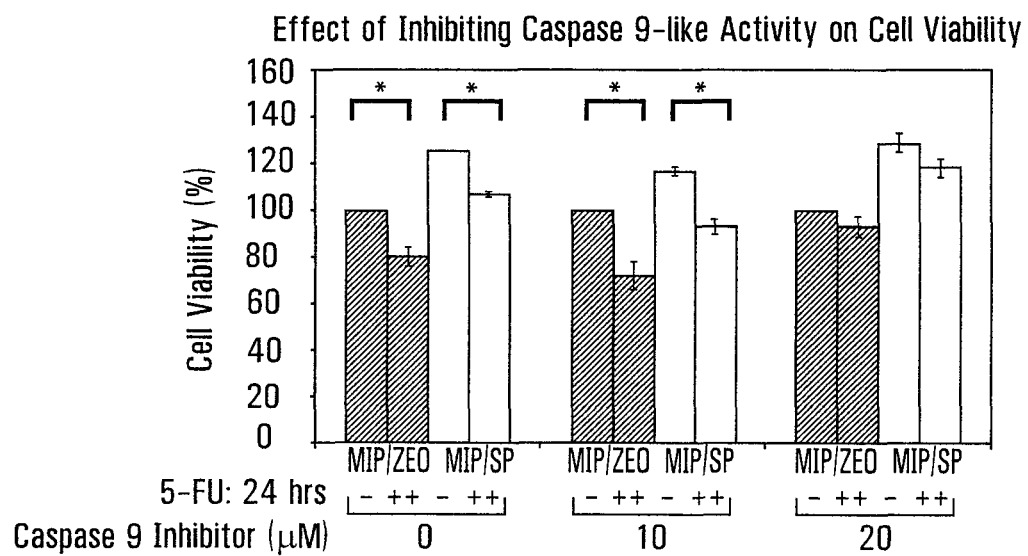

The relative contribution of the extrinsic or intrinsic pathways were examined in SPARC-mediated apoptosis by assessing the effect of Caspase 8 or 9 inhibition on cell viability following in vitro exposure to 5-FU. Using chemical inhibitors that display some specificity against Caspase 8-like (z-IETD-fmk) and Caspase 9-like (z-LEHD-fmk•TFA) activities, it was observed that inhibition of Caspase 8-like activity affected MIP/SP cells more dramatically than control MIP/ZEO cells. In response to 1000 µM of 5-FU for 24 hours only, cell viability decreased by 21.0±5.9% (p=0.0037) in control MIP/ZEO cells and 16.8±4.5% (p=0.0195) in MIP/SP cells (FIG. 3D). However, in MIP/SP cells, pre-incubation with a Caspase 8-like inhibitor prevented a significant decrease in cell viability observed following treatment with 5-FU (FIG. 3D). Cell viability of MIP/SP cells remained unchanged in the presence or absence of 5-FU, while a decrease in cell viability of 14.0±4.6% (p=0.048) could still be observed in the 5-FU-treated MIP/ZEO cells. This increase in cell viability in MIP/SP cells despite the presence of 5-FU could be seen following inhibition with as low as 10 µM of Caspase 8-like inhibitor (data not shown), while no such effect could be demonstrated with a higher concentration of the inhibitor (50 µM) in MIP/ZEO cells. Inhibition of the intrinsic pathway with Caspase 9-like inhibitor desensitized both MIP/ZEO and MIP/SP cells to the effects of chemotherapy by preventing a significant decrease in cell viability in response to 5-FU (FIG. 3D). These results again demonstrate that there is additional involvement of Caspase 8 in diminishing cell viability in the presence of higher levels of SPARC.

Figure 4A:
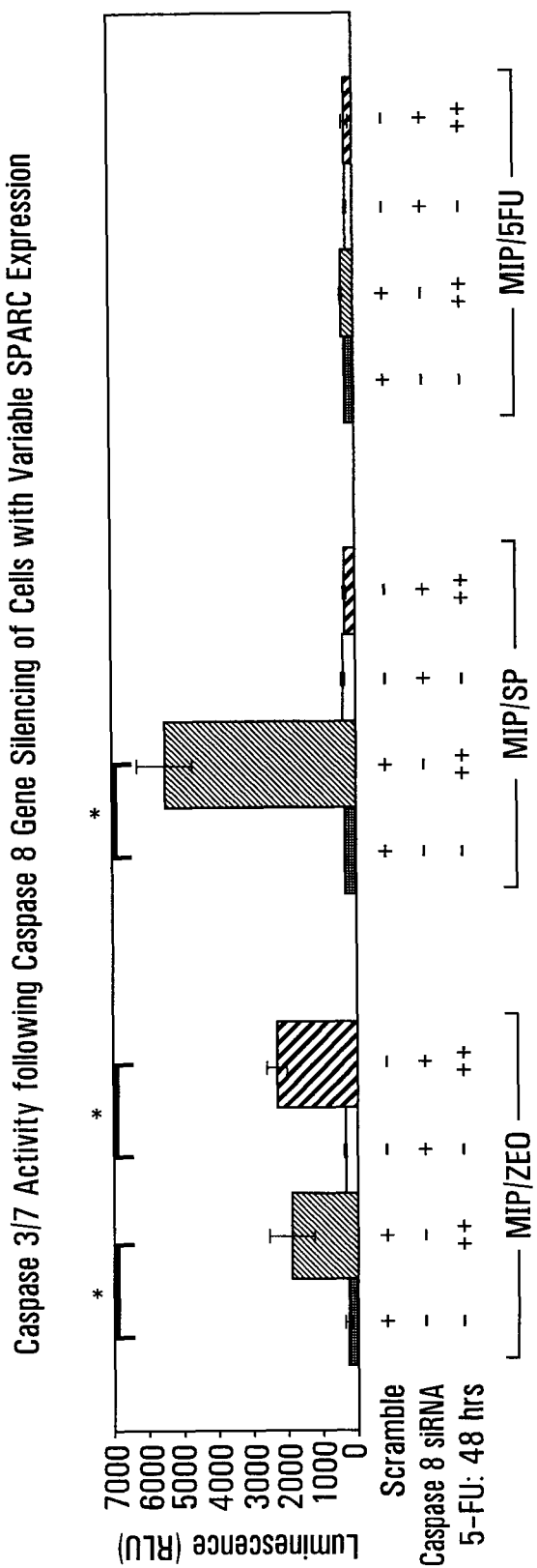
FIG. 4: Inhibition of Caspase 8 gene expression with siRNA enhances survival of cells expressing higher levels of SPARC following exposure to 5-FU.

Given that Caspase 8 gene expression knock-down lessened the effect of 5-FU and CPT-11, and enhanced cell viability in MIP/SP cells, it was next examined whether this resulted from a reduction in apoptosis. Caspase 3/7 activity was similar in MIP/ZEO cells following incubation with 5-FU regardless of whether cells were transfected with Caspase 8 siRNA (2321.3±661.3) or not (scramble control: 1915.0±661.3; p=0.27). However, in MIP/SP cells, an increase in Caspase 3/7 activity was only observed in control MIP/SP cells (untreated 327.7±30.9 vs. 5-FU treated 5501.0±800.0, p=0.0001), and this effect was abrogated when treated cells were initially transfected with Caspase 8 siRNA (untreated 371.0±58.9 vs. treated 291.0±34.7, p=0.31). No Caspase 3 activation was observed in MIP/5FU cells following incubation with 5-FU, either following transfection with Caspase 8 siRNA or scramble control (FIG. 4A).

Figure 4B:
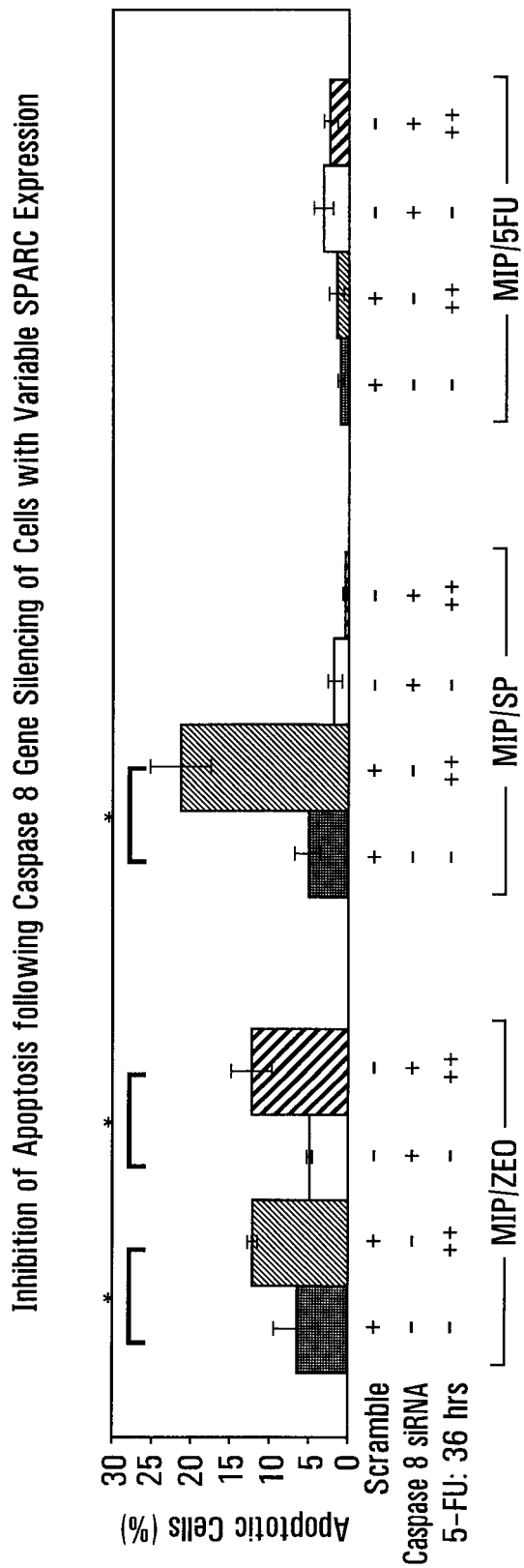
Figure 4C:
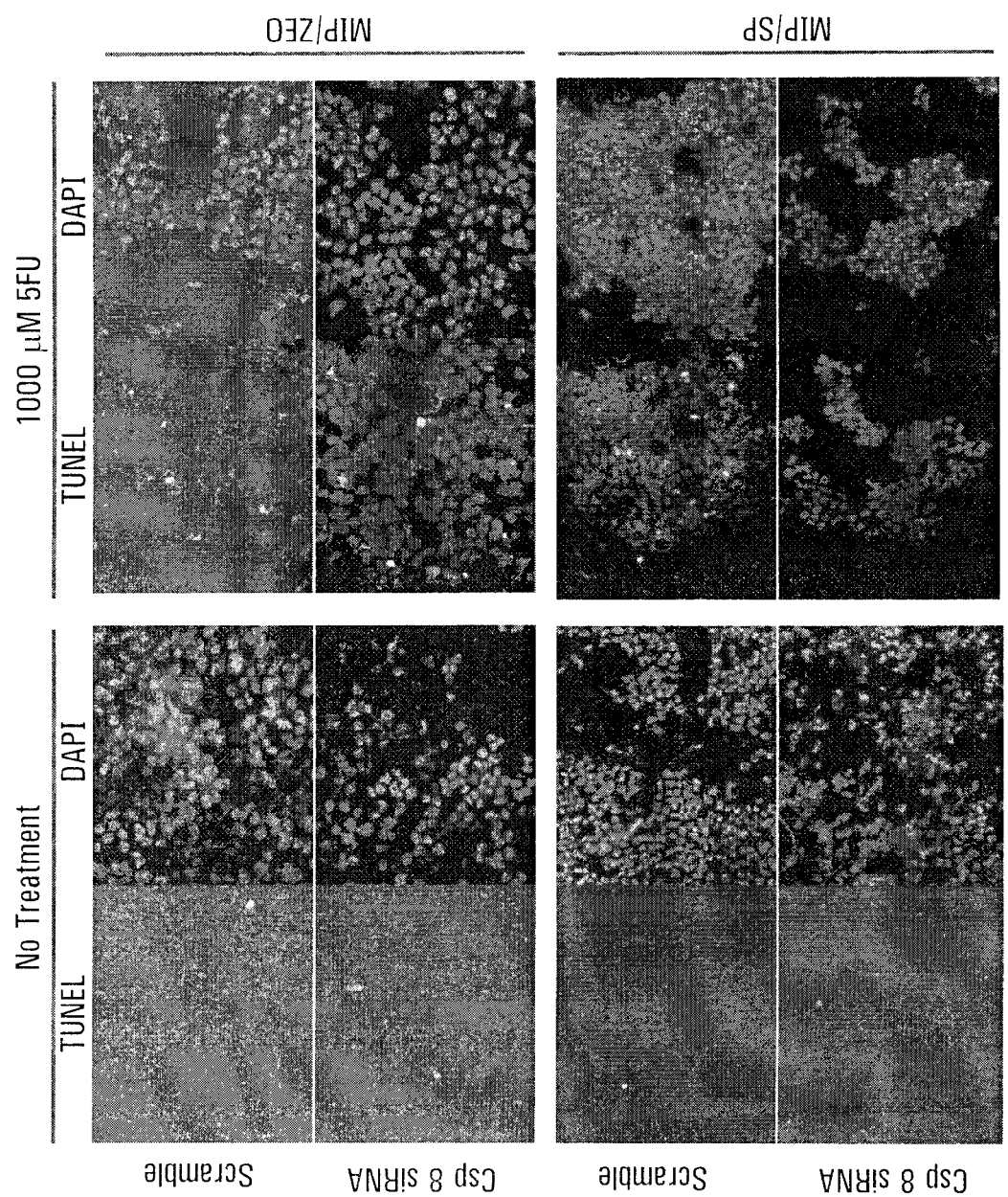

This reduction in apoptosis was further confirmed by TUNEL assay. In the absence of any Caspase 8 inhibition, the highest percentage of cells to undergo apoptosis was observed with MIP/SP cells exposed to 5-FU, with 20.7±6.9% apoptotic cells, in comparison to the untreated group (5.1±2.0%, p=0.0003). However, following Caspase 8 gene knock-down, there was a decrease in the sensitivity of MIP/SP cells to 5-FU (FIG. 4B), with only 0.5±0.5% apoptotic MIP/SP cells detected. A large percentage of MIP/ZEO cells continued to undergo apoptosis regardless of the presence or absence of Caspase 8 gene expression following 5-FU treatment (no transfection with Caspase 8 siRNA: 12.2±0.7% apoptotic cells versus transfection with Caspase 8 siRNA: 12.5±2.4%, p=0.02). Therefore, in complete contrast to MIP/SP cells, knock-down of Caspase 8 did not inhibit apoptosis in MIP/ZEO cells (FIG. 4B, C). Resistant MIP/5FU cells did not respond to 5-FU treatment significantly and this was not influenced by changing the expression of Caspase 8 gene expression (FIG. 4B, C).

Based on the above results, there is recruitment of the extrinsic pathway in SPARC-mediated apoptosis, and in particular, this is associated with a prominent role for Caspase 8. This possibility of a direct SPARC-caspase 8 interaction was examined by assessing binding interactions with SPARC by coimmunoprecipitation studies using antibodies to SPARC, DR4, FADD and Procaspase 8. Different subcellular fractions were examined and only pro-caspase 8 co-immunoprecipitated with SPARC in a reciprocal fashion from the cell membrane (FIG. 5A). This interaction between Procaspase 8 and SPARC disappears when MIP/SP cells were treated with 1000 μM 5-FU (FIG. 5A), when co-immunoprecipiation was performed using an anti-caspase 8 antibody that recognizes the carboxy-terminal sequence of the p18 fragment of the protein. In the high SPARC-expressing HCT116 cells, a similar interaction between pro-caspase 8 and SPARC was observed at the cell membrane (FIG. 5B).

Figure 6A:
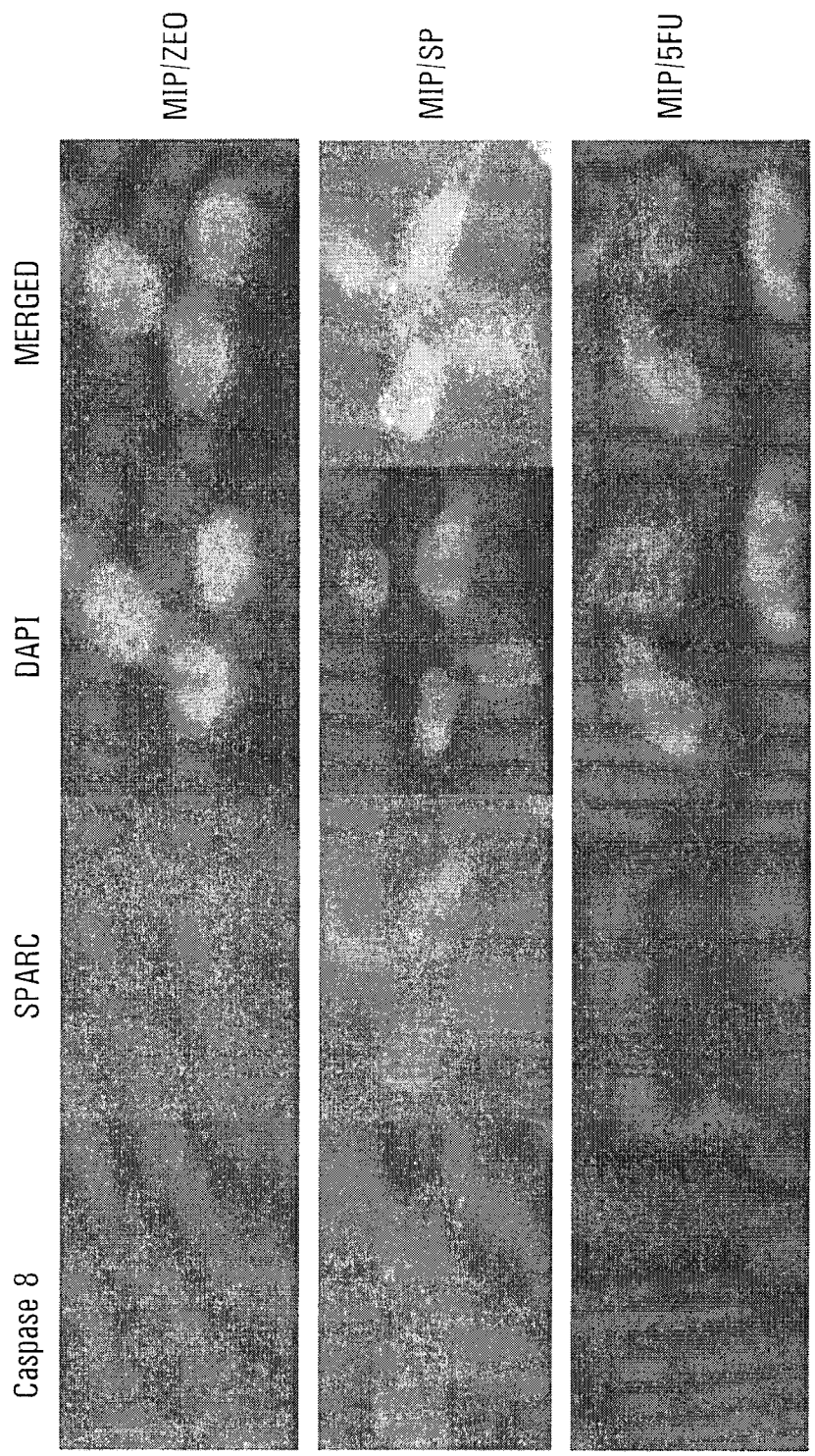
FIG. 6: Caspase 8 is up-regulated in response to overexpression of SPARC in vitro and in tumor xenografts following treatment with a combination of SPARC and 5-FU in vivo.
Figure 6D:
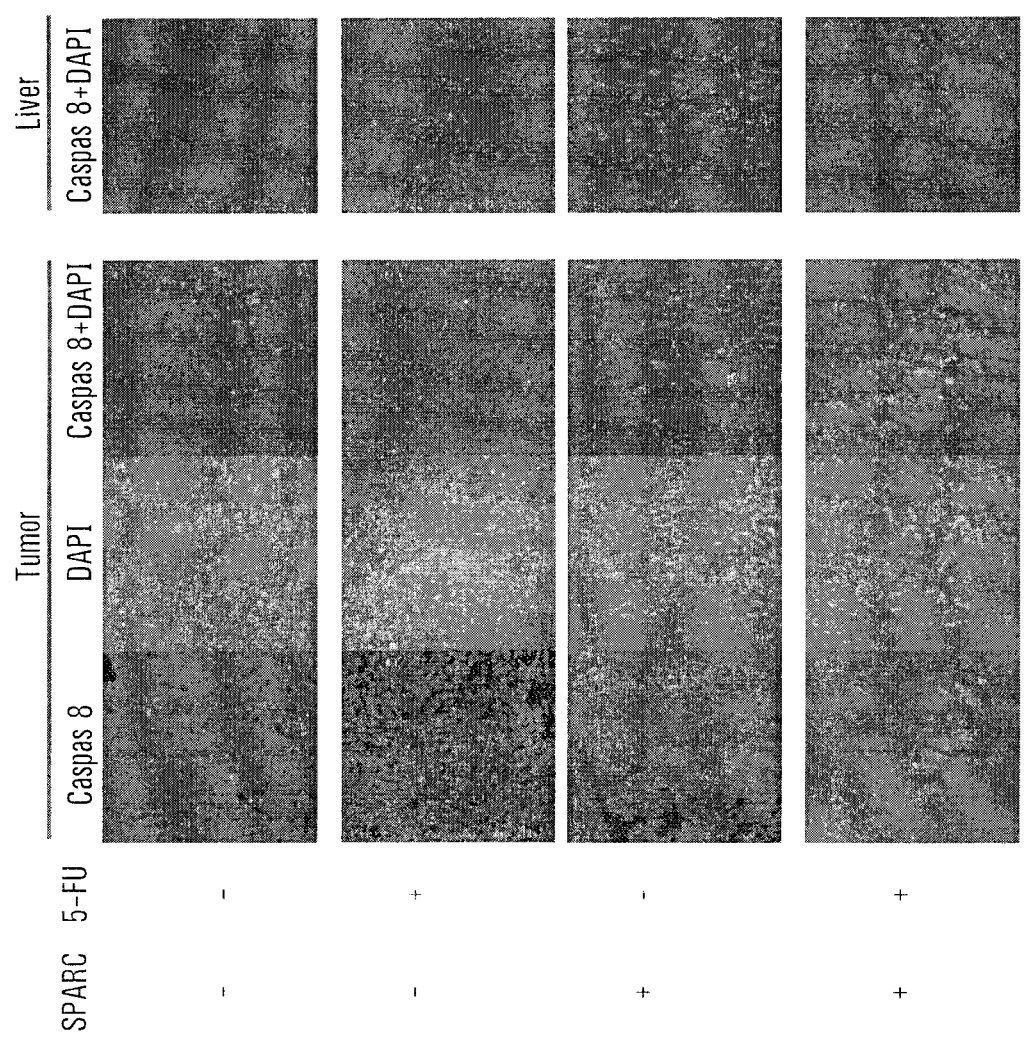

Immunofluorescence staining for SPARC and Caspase 8 were also most prominent in MIP/SP cells and revealed co-localization of SPARC and Caspase 8 expression in the periphery of the cell (FIG. 6A), consistent with our co-immunoprecipitation results. MIP/ZEO and MIP/5FU cells showed minimal SPARC and Caspase 8 expression. SPARC in combination with 5-FU increases Caspase 8 expression in tumor xenografts. Whether the interaction between SPARC and Caspase 8 could also be detected in vivo was next examined. Tumor xenografts bearing MIP/SP cells showed intrinsically higher levels of Caspase 8 gene expression than MIP/ZEO cells (FIG. 6B). Moreover, Caspase 8 protein activity was highest in MIP/SP tumors harvested from animals treated with 5-FU (FIG. 6C). We also examined tumors from MIP 101 mouse xenografts that had been previously treated with a combination of SPARC and 5-FU, or also as single agents, for Caspase 8 expression, and again, only observed higher levels of Caspase 8 in tumor xenografts harvested from mice that were administered SPARC, and even more significantly following combination treatment with SPARC and 5-FU (FIG. 6D). This up-regulation of Caspase 8 expression in animals exposed to both SPARC and 5-FU appears to be restricted to the tumor xenografts, since livers harvested from mice subjected to this treatment did not have elevated Caspase 8 expression (FIG. 6D).

EXAMPLE 6

This Example further localizes the SPARC binding site within the procapse 8 amino acid sequence.
1. Methods Cell Lines: MIP101 and HCT116 (ATCC) human CRC cells were maintained in DMEM media supplemented with 1% penicillin-streptomycin, 1% kanamycin (Invitrogen) and 10% newborn calf serum at 37° C. and 5% $CO_2$. For MIP101 cells resistant to 5-FU (MIP/5FU) or CPT-11 (MIP/CPT), media were also supplemented with 500 μM 5-FU or 10 μM CPT-11, respectively. MIP101 transfected with empty vector (MIP/ZEO) and MIP101 cells stably transfected with SPARC (MIP/SP), were also supplemented with 0.01% zeocin (Invitrogen).

Immunoprecipitation: MIP/SP and HCT116 cells were grown until ~80% confluence, incubated with 1000 μM 5-FU and isolated at 4 hrs. Cells were separated into nuclear, cytosolic, and membrane fractions using ProteoExtract Subcellular Proteome Extraction Kit (EMD Biosciences Inc.). In addition, in order to verify the site of interaction of Caspase 8 with SPARC, MIP/SP and MIP/ZEO cells were also incubated with antibodies against Caspase 8 targeting its C-terminus (Cell Signaling) or N-terminus (Abcam) in vitro for 24 hours at 1.5-3.0 μg prior to collecting and fractionating the cell lysates, for immunoprecipitation, and as well, Caspase 3/7 assay (as described previously). 250 m of the individual cellular fractions were incubated with antibodies against SPARC (10 μg/mL, Haematologic Technologies), Caspase 8 (1:100, Cell Signaling Technology (C-terminus) or Abcam (N-terminus)) or a non-specific anti-mouse IgG antibody as control (Cell Signaling Technologies), in PBS overnight (4° C.) with gentle agitation. Protein:Antibody mixture was then incubated with 304 of Protein A: Protein G (Sigma) (1:1) beads for 4 hrs (4° C.). Proteins were also incubated with EZView Red His-Select HC Nickel affinity gel (Sigma) for immunoprecipitation of His-tagged SPARC protein. For all complexes, beads were washed 5×3 with PBS, eluted with 40 μL of 2×SDS-Loading Buffer, and used for immunoblotting against SPARC and Caspase 8.

2. Results

Figure 7A:
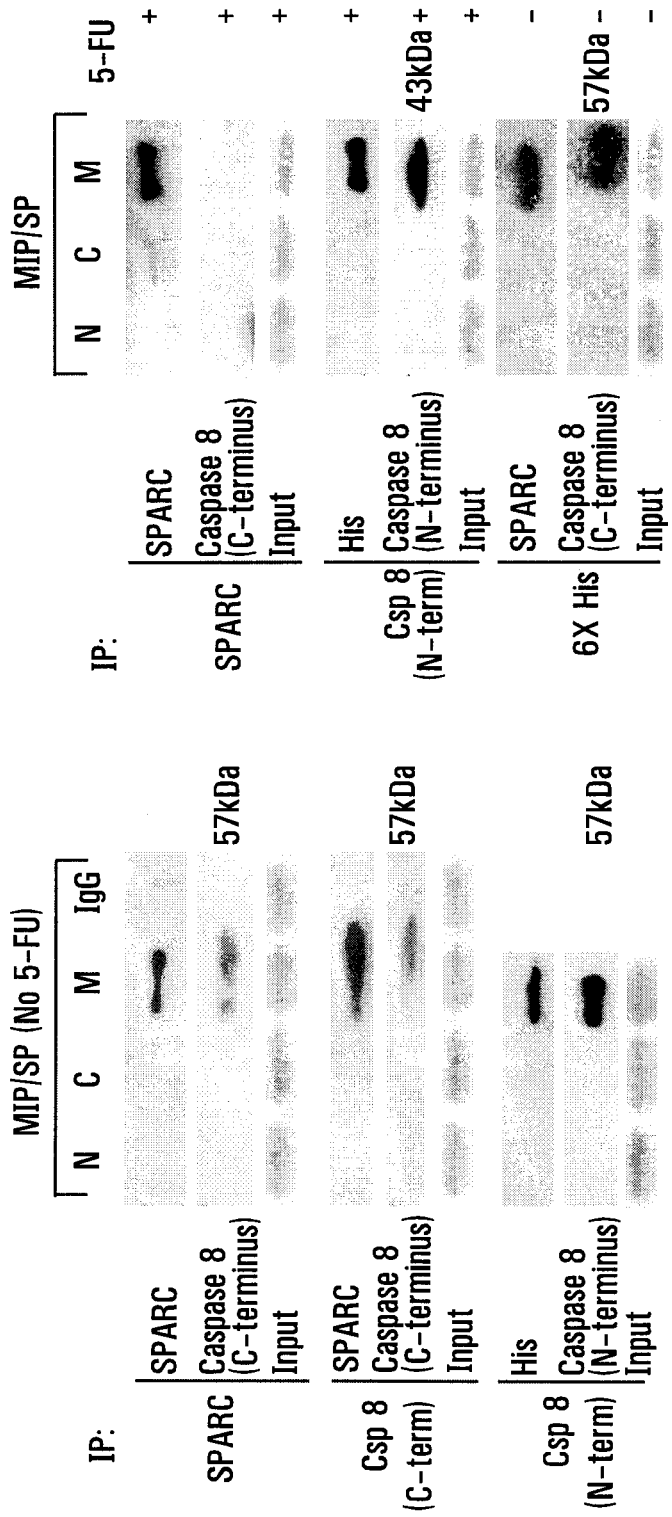
FIG. 7: Interaction between Procaspase 8 and SPARC is disrupted by an antibody to the Procaspase 8 amino terminal domain.
Figure 7B:
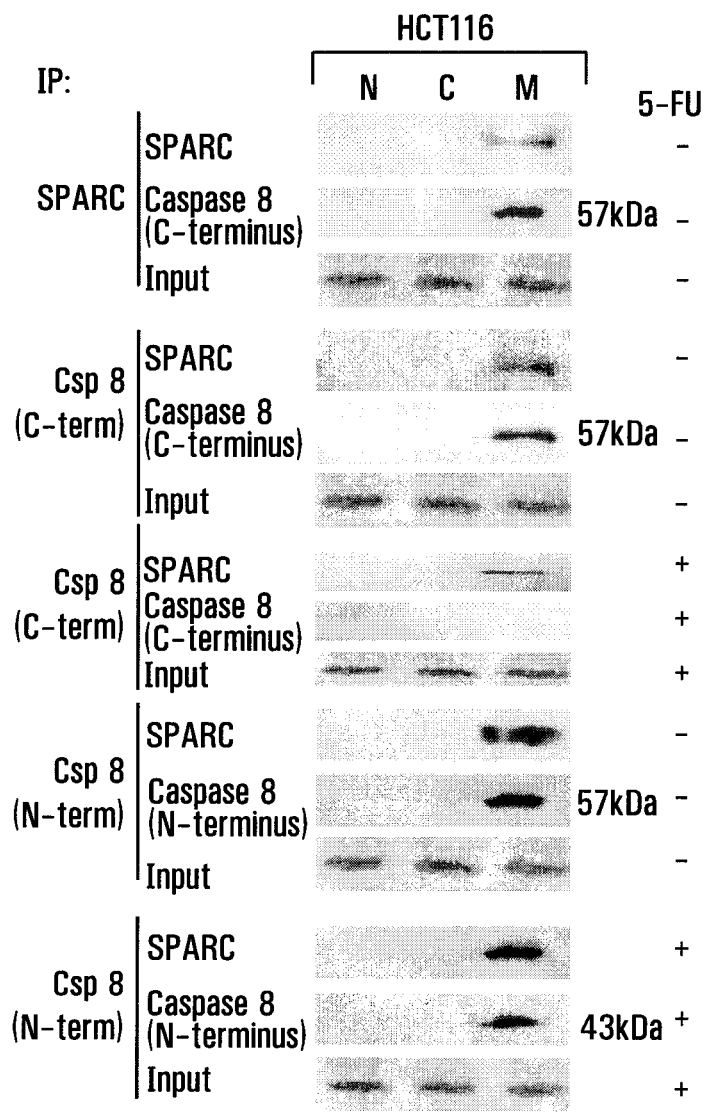

The intramolecular localization of the binding interactions between Procaspase 8 and SPARC was further studied by co-immunoprecipitation using antibodies different regions of Procaspase 8. Different subcellular fractions were examined by Procaspase 8 co-IP with SPARC in a reciprocal fashion from the MIP/SP (FIG. 7A) and intrinsically SPARC-overexpressing HCT116 cell membrane fractions (FIG. 7B). Surprisingly, the ability to co-IP of Procaspase 8 and SPARC disappeared when MIP/SP cells were exposed to 1000 μM 5-FU (which induces Procaspase 8 cleavage) and an anti-caspase 8 antibody that recognizes the carboxy-terminal sequence of the p18 fragment of the protein was used (FIG. 7A). In contrast, using an anti-caspase 8 antibody recognizing the N-terminal region of this protein, the interaction between SPARC and Procaspase 8 could still be detected despite 5-FU exposure (FIG. 7B).

Figure 7C:
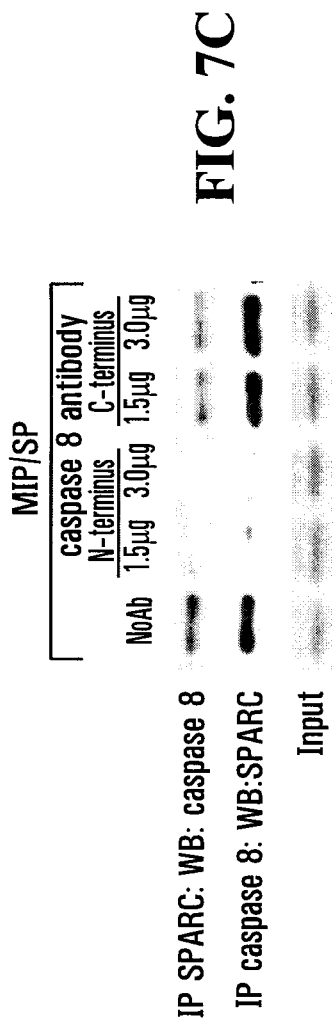
Figure 7D:
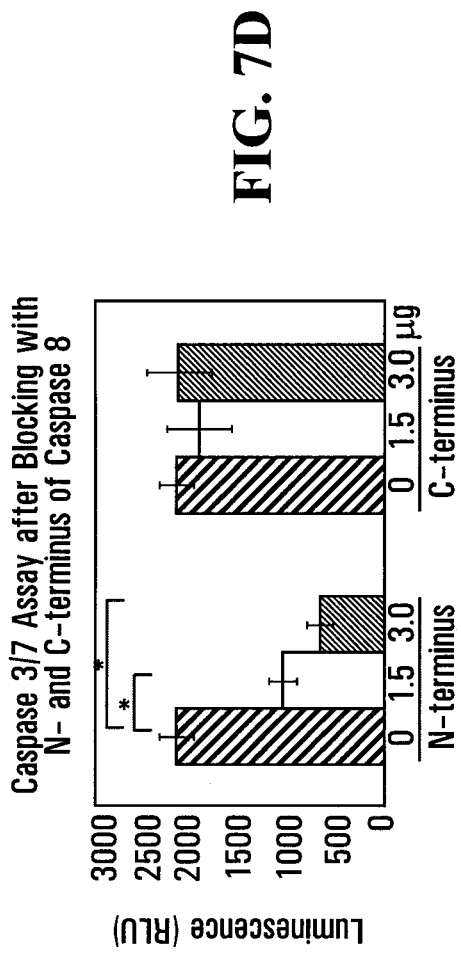

In order to further validate that the interaction between SPARC and Procaspase 8 occurs within the N-terminus region of Procaspase 8, MIP/SP cells were incubated in vitro with antibodies to Caspase 8 targeting its N- or C-terminus. Cell lysates subjected to reciprocal co-IP with SPARC or Caspase 8 showed that cells incubated with antibodies targeting the N-terminus of Caspase 8 no longer interacted with SPARC, while incubation with antibodies targeting the C-terminus had no such effect (FIG. 7C). By interfering with this interaction, MIP/SP cells became less responsive to 5-FU as indicated by a significant reduction in apoptosis (FIG. 7D).

Figure 7E:
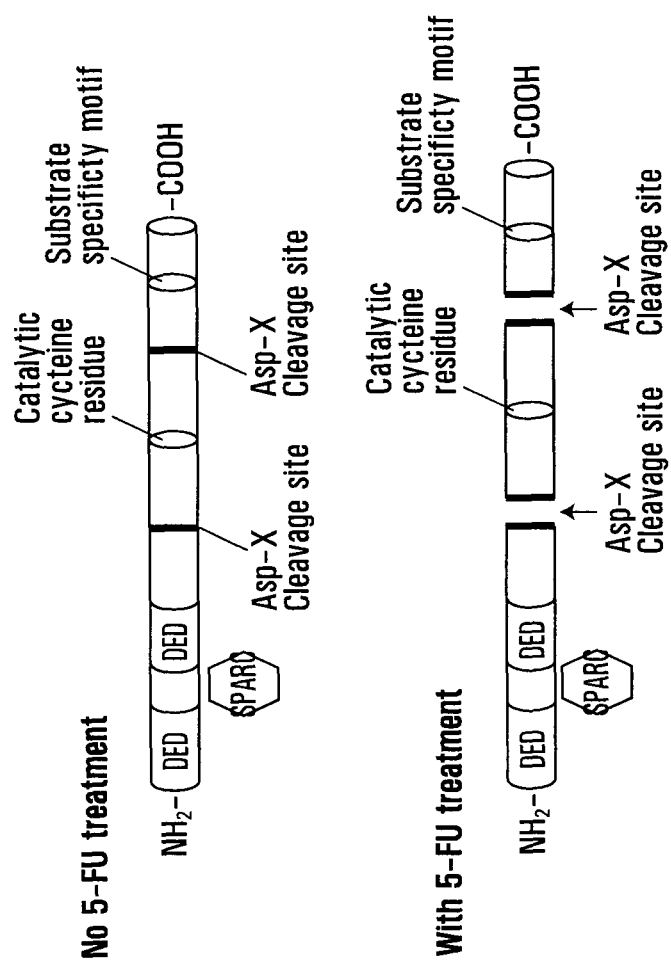

Thus, this Example demonstrates an interaction between SPARC and Procaspase 8, taking place at the amino p43/p41 fragment of Caspase 8 containing the N-terminal DED-domains and the catalytic site (FIG. 7E).

EXAMPLE 7

This example demonstrates that Procaspase 8 binds to a SPARC domain which is amino (upstream) of the SPARC follistatin-like domain domain.

Figure 8A:
FIG. 8: Interaction between Procaspase 8 and SPARC occurs within a specific SPARC domain.
Figure 8B:
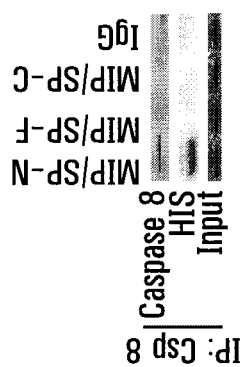

Immunoprecipation was performed with anti-histidine tag antibody (IP: His) (See FIG. 8A) or an anti-Caspase 8 antibody (IP: Capsaase 8) (See FIG. 8B) in the presence of Procaspase 8 and truncated SPARC polypeptides comprising a sequence near the SPARC amino terminus (SEQ ID NO: 20) (MIP/NT), a sequence from the SPARC follistatin-like domain (SEQ ID NO: 22) (MIP/FS), a sequence from the SPARC extracellular domain (SEQ ID NO: 24) (MIP/EC) or a control antibody (IgG). These studies confirm that the interaction between SPARC and Procaspase 8 is specific and involves a SPARC domain which is within the amino acid sequence of SEQ ID NO: 20.

EXAMPLE 8

This example demonstrates that Bcl-2 interacts with Procaspase 8 and that the site of interaction between Bcl-2 and Procaspase 8 is in the same region where SPARC interacts with Procaspase 8. This example further demonstrates that loss of Bcl-2 binding to Procaspase 8 by SPARC results in increased sensitivity of cells to chemotherapy.

The cell lines MIP101, RKO, MiaPaca, and MCF-7 cells were maintained in DMEM media supplemented with 1% penicillin-streptomycin, 1% kanamycin (Invitrogen) and 10% newborn calf serum at 37° C. and 5% $CO_2$. For MIP101 cells resistant to 5-FU (MIP/5FU) or CPT-11 (MIP/CPT), media were also supplemented with 500 µM 5-FU or 10 µM CPT-11, respectively. For RKO cells resistant to 5-FU (RKO/5FU), or CPT-11 (RKO/CPT), media were also supplemented with 25 µM 5-FU, or 18 µM CPT-11, respectively. For MiaPaca cells resistant to CPT, media was also supplemented with 100 µM CPT-11. For MCF-7 cells resistant to cisplatin, media was supplemented with 30 µM cisplatin. MIP 101 transfected with empty vector (MIP/ZEO) or MIP 101 cells stably transfected with SPARC (MIP/SP), were also supplemented with 0.01% zeocin (Invitrogen).

Cells were grown until ~80% confluence, and lysates were separated into nuclear, cytosolic, and membrane fractions. 250 µg of individual cellular fractions were incubated with antibodies against HIS (1:100, Sigma), capsase 8 (N-terminus) (1:100, Abcam), Bcl-2 (1:100, Cell Signaling Technologies) or a non-specific anti-mouse IgG antibody as control (Cell Signaling Technologies), in PBS overnight (4° C.). Protein:Antibody mixture was then incubated with 30 mL of Protein A:Protein G (Sigma) (1:1) beads for 4 hours (4° C.). For all complexes, beads were washed with PBS, and eluted with 2×SDS-loading buffer, and used for immunoblotting against caspase 8, HIS, or Bcl-2.

In order to determine the region of interaction between Bcl-2 and Procaspase 8, cells were also incubated with antibodies against caspase 8 targeting its C-terminus (Cell Signaling) or N-terminus (Abeam) in vitro for 24 hours at 1.5-3.0 µg prior to collecting and fractionating the cell lysates for immunoprecipitation. In addition, to assess if exogenous SPARC interferes with the interaction of procaspase 8 and Bcl-2, cells were incubated with 10 µg/ml of SPARC for 72-hrs, in the presence or absence of antibodies against SPARC (3 µg, Hematologic Technologies) for 24 hrs, prior to collection for cellular fractionation and immunoprecipitation.

In resistant cell lines (MIP101 colorectal cancer cells resistant to 5-FU, MIP/5FU; pancreatic cancer cells resistant to CPT, MiaPaca/CPT), these studies demonstrate that Bcl-2 interacts with Procaspase 8 (FIGS. 9A and 9C). It is further demonstrated that this interaction between Bcl-2 and Procaspase 8 can be blocked by the use of antibodies directed toward the N-terminus of Procapase 8 (FIG. 9B) and as well, with the addition of exogenous SPARC (FIG. 9C). It is further demonstrated that interference of Bcl-2 binding to Procaspase 8 by SPARC results in increased cellular chemotherapeutic sensitivity.

EXAMPLE 9

This example demonstrates that the interaction between Bcl-2 and Procaspase 8 occurs in the region of the DEDI and DEDII domains of Procaspase 8.

Site-directed mutagenesis was carried out as follows: Procaspase 8 cDNA was cloned into pcDNA3.1/myc-His. 100 ng of plasmid DNA was methylated with DNA methylase (4 U/µL) and 10×SAM's buffer as per manufacturer's protocol (Gene Tailor Site-Directed Mutagenesis system, Invitrogen) for 1 hour at 37° C. Methylated DNA was then subjected to mutagenesis, using the following specific primers to target mutations within the DEDI domain (forward 5' tctttagaaa tactataacc AGGTACCATC AGGTACCGTG tagaccggag 3', reverse 5' ggttatagta tttctaaaga cgacttcagg 3'); putative binding (PB) region (forward 5' ttgac ctgtcacttc tagaAATAGC ggagttcaag 3', reverse 5' tctagaagtgacag gtcaacaagg ggtt 3'); and DEDII domain (forward 5' gagatagtct aaagtcttct CCTAGTACAG GAGCTAACTC ccagaaaatt 3', reverse 5' agaagacttt agctatctc gtactgggac 3'). All mutations were verified by DNA sequencing. Once verified, vectors expressing either the wild type procaspase 8 (Csp 8), or the mutant procaspase 8 with mutations in the DEDI domain (DEDI), protein binding domain (PB) or DEDII domain (DEDII) were then used for transient transfection into cells.

Figure 10A:
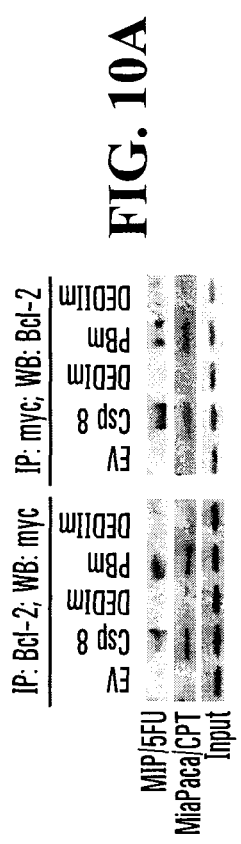
FIG. 10: Interaction between Bcl-2 and Procaspase 8 occurs in the region of the DEDI and DEDII domains of Procaspase 8.
Figure 10B:
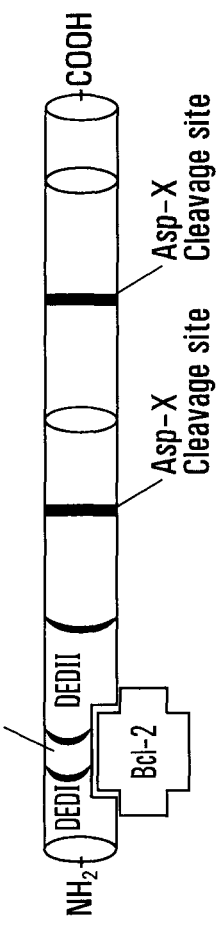

The cell lines and cell lysate procedures described in Example 8 were used in Example 9. The site-directed mutagenesis studies demonstrated that mutations to the DEI and DEDII domains of Procaspase 8 abolished the ability of Procaspase 8 to bind with Bcl-2 (FIG. 10A). In particular, as demonstrated in FIG. 10A, transient transfection of MIP/5FU and MiaPaCa/CPT with vectors containing Procaspase 8 with mutations wither within the DEDI or DEDII domains failed to immunoprecipitate Bcl-2 in a reciprocal fashion as compared with cells transfected with wild-type Procaspase 8. A potential model for the interaction between Procaspase 8, SPARC, and Bcl-2 is provided in FIG. 10B.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition, the composition comprising a therapeutic or diagnostic agent coupled to a Pro-caspase 8 polypeptide and a pharmaceutically acceptable carrier, wherein the therapeutic or diagnostic agent is for the treatment or diagnosis of a cancer, and wherein the Pro-caspase 8 polypeptide comprises an amino acid sequence of any one of SEQ ID NOS: 1-18, 25, and 26.

2. The pharmaceutical composition of claim 1, wherein the diagnostic agent is selected from the group consisting of radioactive agents, MRI contrast agents, X-ray contrast agents, ultrasound contrast agents, and PET contrast agents.

3. The pharmaceutical composition of claim 1, wherein the therapeutic agent is selected from the group consisting of docetaxel, paclitaxel, taxanes, platinum compounds, anti-folates, antimetabolites, antimitotics, DNA damaging agents, proapoptotics, differentiation inducing agents, antiangiogenic agents, antibiotics, hormones, peptides, antibodies, tyrosine kinase inhibitors, kinase inhibitors, anti-vascular endothelial growth factor compounds (anti-VEGFs), anti-epidermal growth factor receptor compounds (anti-EGFRs), tTF, TNF, radionuclides, and combinations thereof.

4. The pharmaceutical composition of claim 1, wherein the therapeutic agent is selected from the group consisting of genistein, adriamycin, ansamycin, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, melphalan, methotrexate, rapamycin (sirolimus), mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinoreibine, taxol, combretastatins, discodermolides, transpiatinum, 5-fluorouracil radionuclides, and combinations thereof.

5. The pharmaceutical composition of claim 3, wherein the therapeutic agent comprises particles of paclitaxel and wherein more than 50% of the therapeutic agent is in nanoparticle form.

6. The pharmaceutical composition of claim 3, wherein the therapeutic agent is an antibody or antibody fragment which mediates one or more of complement activation, cell mediated cytotoxicity, and opsinization.

7. A method for delivering a therapeutic or diagnostic agent to a disease site in a mammal, wherein the disease is cancer, wherein said method comprises administering to the mammal a therapeutically or diagnostically effective amount of a pharmaceutical composition of claim 1.

8. The method of claim 7, wherein the mammal is a human.

9. The method of claim 7, wherein the disease site is a tumor.

10. The method of claim 9, wherein the tumor is located in the lung, prostate, head, neck, bladder, liver, ovary, kidney, gut, brain, or breast.

11. The method of claim 7, wherein the route of administration is selected from the group consisting of intravenous, subcutaneous, intramuscular, intraperitoneal, intratumoral, oral, and inhalational.

12. The method of claim 7, wherein the diagnostic agent is selected from the group consisting of radioactive agents, MRI contrast agents, X-ray contrast agents, ultrasound contrast agents, and PET contrast agents.

13. The method of claim 7, wherein the therapeutic agent is selected from the group consisting of docetaxel, paclitaxel, taxanes, platinum compounds, antifolates, antimetabolites, antimitotics, DNA damaging agents, proapoptotics, differentiation inducing agents, antiangiogenic agents, antibiotics, hormones, peptides, antibodies, tyrosine kinase inhibitors, kinase inhibitors, anti-vascular endothelial growth factor compounds (anti-VEGFs), anti-epidermal growth factor receptor compounds (anti-EGFRs), tTF, TNF, radionuclides, and combinations thereof.

14. The method of claim 13, wherein the therapeutic agent is selected from the group consisting of genistein, adriamycin, ansamycin, asparaginase, bleomycin, busulphan, cisplatin, carboplatin, carmustine, capecitabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, melphalan, methotrexate, rapamycin (sirolimus), mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, 5-fluorouracil, radionuclides, and combinations thereof.

15. The method of claim 13, wherein the therapeutic agent comprises particles of paclitaxel and wherein more than 50% of the therapeutic agent is in nanoparticle form.

16. The method of claim 13, wherein the therapeutic agent is an antibody or antibody fragment which mediates one or more of complement activation, cell mediated cytotoxicity, and opsinization.

17. A kit for diagnosing or treating a disease in a mammal wherein said kit comprises a pharmaceutical composition of claim 1; and instructions for use in the diagnosis and/or treatment of cancer.

18. The method of claim 9, wherein the tumor is selected from oral cavity tumors, pharyngeal tumors, digestive system tumors, the respiratory system tumors, bone tumors, cartilaginous tumors, bone metastases, sarcomas, skin tumors, melanoma, breast tumors, the genital system tumors, urinary tract tumors, orbital tumors, brain and central nervous system tumors, gliomas, endocrine system tumors, thyroid tumors, esophageal tumors, gastric tumors, small intestinal tumors, colonic tumors, rectal tumors, anal tumors, liver tumors, gall bladder tumors, pancreatic tumors, laryngeal tumors, tumors of the lung, bronchial tumors, non-small cell lung carcinoma, small cell lung carcinoma, uterine cervical tumors, uterine corpus tumors, ovarian tumors, vulvar tumors, vaginal tumors, prostate tumors, prostatic carcinoma, testicular tumors, tumors of the penis, urinary bladder tumors, tumors of the kidney, tumors of the renal pelvis, tumors of the ureter, head and neck tumors, parathyroid cancer, Hodgkin's disease, Non-Hodgkin's lymphoma, multiple myeloma, leukemia, acute lymphocytic leukemia, chronic lymphocytic leukemia, acute myeloid leukemia, chronic myeloid leukemia, and a combination thereof.

19. The method of claim 9, wherein the tumor is a sarcoma, adenocarcinoma, squamous cell carcinoma, large cell carcinoma, small cell carcinoma, basal cell carcinoma, clear cell carcinoma, oncytoma, or a combination thereof.

20. The method of claim 7, wherein the cancer is colorectal cancer.

21. The method of claim 7, wherein the cancer is breast cancer.

22. The method of claim 7, wherein the cancer is head and neck cancer.

23. The method of claim 7, wherein the cancer is non-small cell lung cancer.

24. The method of claim 7, wherein the cancer is pancreatic cancer.

25. The method of claim 7, wherein the cancer is melanoma.

26. The method of claim 7, wherein the cancer is bladder cancer.

* * * * *

UNITED STATES PATENT AND TRADEMARK OFFICE
CERTIFICATE OF CORRECTION

PATENT NO. : 8,778,302 B2
APPLICATION NO. : 12/530504
DATED : July 15, 2014
INVENTOR(S) : Isabella Tai It is certified that error appears in the above-identified patent and that said Letters Patent is hereby corrected as shown below:

In the Specification

Column 2,
Line 36, "stimuli.," should read --stimuli,--.

Column 14,
Line 15, "Esophagus 5/5" should read --Esophagus 5/5--.

Column 14,
Line 25, "Kidney (F) 6/8" should read --Kidney (F) 6/8--.

Column 16,
Line 13, "(VIIP/ZEO)" should read --(MIP/ZEO)--.

Column 17,
Line 48, "(z-LEHDfink ·" should read --(z-LEHDfmk ·--.

Column 18,
Line 28, "in a E-well plate," should read --in a 6-well plate,--.

Column 19,
Line 23, "with 100004" should read --with 1000μM--.

Column 22,
Line 22, "250 m of" should read --250μg of--.

Column 22,
Line 29, "with 304" should read --with 30μL--.

Signed and Sealed this
Sixteenth Day of December, 2014

Michelle K. Lee
*Deputy Director of the United States Patent and Trademark Office*

Column 66,
Line 59, "vinoreibine," should read --vinorelbine,--.

Column 66,
Line 60, "transpiatinum," should read --transplatinum,--.

SEQUENCE LISTING

```
<160> NUMBER OF SEQ ID NOS: 44

<210> SEQ ID NO 1
<211> LENGTH: 171
<212> TYPE: PRT
<213> ORGANISM: Homo sapiens

<400> SEQUENCE: 1

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu
                165                 170

<210> SEQ ID NO 2
<211> LENGTH: 353
<212> TYPE: PRT
<213> ORGANISM: Homo sapiens

<400> SEQUENCE: 2

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
```

```
                65                  70                  75                  80
Thr Arg Lys Glu Glu Met Glu Arg Glu Leu Gln Thr Pro Gly Arg Ala
                    85                  90                  95
Gln Ile Ser Ala Tyr Arg Val Met Leu Tyr Gln Ile Ser Glu Glu Val
                    100                 105                 110
Ser Arg Ser Glu Leu Arg Ser Phe Lys Phe Leu Leu Gln Glu Glu Ile
                    115                 120                 125
Ser Lys Cys Lys Leu Asp Asp Met Asn Leu Leu Asp Ile Phe Ile
                130                 135                 140
Glu Met Glu Lys Arg Val Ile Leu Gly Glu Gly Lys Leu Asp Ile Leu
145                 150                 155                 160
Lys Arg Val Cys Ala Gln Ile Asn Lys Ser Leu Leu Lys Ile Ile Asn
                    165                 170                 175
Asp Tyr Glu Glu Phe Ser Lys Glu Arg Ser Ser Ser Leu Glu Gly Ser
                    180                 185                 190
Pro Asp Glu Phe Ser Asn Gly Glu Glu Leu Cys Gly Val Met Thr Ile
                    195                 200                 205
Ser Asp Ser Pro Arg Glu Gln Asp Ser Glu Ser Gln Thr Leu Asp Lys
                210                 215                 220
Val Tyr Gln Met Lys Ser Lys Pro Arg Gly Tyr Cys Leu Ile Ile Asn
225                 230                 235                 240
Asn His Asn Phe Ala Lys Ala Arg Glu Lys Val Pro Lys Leu His Ser
                    245                 250                 255
Ile Arg Asp Arg Asn Gly Thr His Leu Asp Ala Gly Ala Leu Thr Thr
                    260                 265                 270
Thr Phe Glu Glu Leu His Phe Glu Ile Lys Pro His Asp Asp Cys Thr
                    275                 280                 285
Val Glu Gln Ile Tyr Glu Ile Leu Lys Ile Tyr Gln Leu Met Asp His
                    290                 295                 300
Ser Asn Met Asp Cys Phe Ile Cys Cys Ile Leu Ser His Gly Asp Lys
305                 310                 315                 320
Gly Ile Ile Tyr Gly Thr Asp Gly Gln Glu Ala Pro Ile Tyr Glu Leu
                    325                 330                 335
Thr Ser Gln Phe Thr Gly Phe Gly Cys Pro Ser Leu Ala Gly Lys Pro
                    340                 345                 350
Lys

<210> SEQ ID NO 3
<211> LENGTH: 339
<212> TYPE: PRT
<213> ORGANISM: Homo sapiens

<400> SEQUENCE: 3

Met Asp Phe Ser Arg Asn Leu Tyr Asp Ile Gly Glu Gln Leu Asp Ser
1               5                   10                  15
Glu Asp Leu Ala Ser Leu Lys Phe Leu Ser Leu Asp Tyr Ile Pro Gln
                    20                  25                  30
Arg Lys Gln Glu Pro Ile Lys Asp Ala Leu Met Leu Phe Gln Arg Leu
                35                  40                  45
Gln Glu Lys Arg Met Leu Glu Glu Ser Asn Leu Ser Phe Leu Lys Glu
                    50                  55                  60
Leu Leu Phe Arg Ile Asn Arg Leu Asp Leu Leu Ile Thr Tyr Leu Asn
65                  70                  75                  80
Thr Arg Lys Glu Glu Met Glu Arg Glu Leu Gln Thr Pro Gly Arg Ala
```

```
                    85                  90                  95
Gln Ile Ser Ala Tyr Arg Val Met Leu Tyr Gln Ile Ser Glu Glu Val
            100                 105                 110
Ser Arg Ser Glu Leu Arg Ser Phe Lys Phe Leu Leu Gln Glu Glu Ile
            115                 120                 125
Ser Lys Cys Lys Leu Asp Asp Met Asn Leu Leu Asp Ile Phe Ile
            130                 135                 140
Glu Met Glu Lys Arg Val Ile Leu Gly Glu Gly Lys Leu Asp Ile Leu
145                 150                 155                 160
Lys Arg Val Cys Ala Gln Ile Asn Lys Ser Leu Leu Lys Ile Ile Asn
                165                 170                 175
Asp Tyr Glu Glu Phe Ser Lys Gly Glu Glu Leu Cys Gly Val Met Thr
                180                 185                 190
Ile Ser Asp Ser Pro Arg Glu Gln Asp Ser Glu Ser Gln Thr Leu Asp
                195                 200                 205
Lys Val Tyr Gln Met Lys Ser Lys Pro Arg Gly Tyr Cys Leu Ile Ile
            210                 215                 220
Asn Asn His Asn Phe Ala Lys Ala Arg Glu Lys Val Pro Lys Leu His
225                 230                 235                 240
Ser Ile Arg Asp Arg Asn Gly Thr His Leu Asp Ala Gly Ala Leu Thr
                245                 250                 255
Thr Thr Phe Glu Glu Leu His Phe Glu Ile Lys Pro His Asp Asp Cys
            260                 265                 270
Thr Val Glu Gln Ile Tyr Glu Ile Leu Lys Ile Tyr Gln Leu Met Asp
            275                 280                 285
His Ser Asn Met Asp Cys Phe Ile Cys Cys Ile Leu Ser His Gly Asp
            290                 295                 300
Lys Gly Ile Ile Tyr Gly Thr Asp Gly Gln Glu Ala Pro Ile Tyr Glu
305                 310                 315                 320
Leu Thr Ser Gln Phe Thr Gly Leu Lys Cys Pro Ser Leu Ala Gly Lys
                325                 330                 335
Pro Lys Val

<210> SEQ ID NO 4
<211> LENGTH: 93
<212> TYPE: PRT
<213> ORGANISM: Homo sapiens

<400> SEQUENCE: 4

Met Asp Phe Ser Arg Asn Leu Tyr Asp Ile Gly Glu Gln Leu Asp Ser
1               5                   10                  15
Glu Asp Leu Ala Ser Leu Lys Phe Leu Ser Leu Asp Tyr Ile Pro Gln
            20                  25                  30
Arg Lys Gln Glu Pro Ile Lys Asp Ala Leu Met Leu Phe Gln Arg Leu
        35                  40                  45
Gln Glu Lys Arg Met Leu Glu Glu Ser Asn Leu Ser Phe Leu Lys Glu
    50                  55                  60
Leu Leu Phe Arg Ile Asn Arg Leu Asp Leu Leu Ile Thr Tyr Leu Asn
65                  70                  75                  80
Thr Arg Lys Glu Glu Met Glu Arg Glu Leu Gln Thr Pro
                85                  90

<210> SEQ ID NO 5
<211> LENGTH: 479
<212> TYPE: PRT
```

<213> ORGANISM: Homo sapiens

<400> SEQUENCE: 5

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
    370                 375                 380

Leu Ser Ser Pro Gln Thr Arg Tyr Ile Pro Asp Glu Ala Asp Phe Leu
385                 390                 395                 400

```
Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Asp Lys Asn Met Gly Lys Gln Met Pro
    450                 455                 460

Gln Pro Thr Phe Thr Leu Arg Lys Lys Leu Val Phe Pro Ser Asp
465                 470                 475

<210> SEQ ID NO 6
<211> LENGTH: 464
<212> TYPE: PRT
<213> ORGANISM: Homo sapiens

<400> SEQUENCE: 6

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Glu Glu Leu Cys Gly Val Met Thr
            180                 185                 190

Ile Ser Asp Ser Pro Arg Glu Gln Asp Ser Glu Ser Gln Thr Leu Asp
        195                 200                 205

Lys Val Tyr Gln Met Lys Ser Lys Pro Arg Gly Tyr Cys Leu Ile Ile
    210                 215                 220

Asn Asn His Asn Phe Ala Lys Ala Arg Glu Lys Val Pro Lys Leu His
225                 230                 235                 240

Ser Ile Arg Asp Arg Asn Gly Thr His Leu Asp Ala Gly Ala Leu Thr
                245                 250                 255

Thr Thr Phe Glu Glu Leu His Phe Glu Ile Lys Pro His Asp Asp Cys
            260                 265                 270

Thr Val Glu Gln Ile Tyr Glu Ile Leu Lys Ile Tyr Gln Leu Met Asp
        275                 280                 285

His Ser Asn Met Asp Cys Phe Ile Cys Cys Ile Leu Ser His Gly Asp
    290                 295                 300
```

```
Lys Gly Ile Ile Tyr Gly Thr Asp Gly Gln Glu Ala Pro Ile Tyr Glu
305                 310                 315                 320

Leu Thr Ser Gln Phe Thr Gly Leu Lys Cys Pro Ser Leu Ala Gly Lys
                325                 330                 335

Pro Lys Val Phe Phe Ile Gln Ala Cys Gln Gly Asp Asn Tyr Gln Lys
            340                 345                 350

Gly Ile Pro Val Glu Thr Asp Ser Glu Glu Gln Pro Tyr Leu Glu Met
        355                 360                 365

Asp Leu Ser Ser Pro Gln Thr Arg Tyr Ile Pro Asp Glu Ala Asp Phe
    370                 375                 380

Leu Leu Gly Met Ala Thr Val Asn Asn Cys Val Ser Tyr Arg Asn Pro
385                 390                 395                 400

Ala Glu Gly Thr Trp Tyr Ile Gln Ser Leu Cys Gln Ser Leu Arg Glu
                405                 410                 415

Arg Cys Pro Arg Gly Asp Asp Ile Leu Thr Ile Leu Thr Glu Val Asn
            420                 425                 430

Tyr Glu Val Ser Asn Lys Asp Asp Lys Lys Asn Met Gly Lys Gln Met
        435                 440                 445

Pro Gln Pro Thr Phe Thr Leu Arg Lys Lys Leu Val Phe Pro Ser Asp
    450                 455                 460

<210> SEQ ID NO 7
<211> LENGTH: 395
<212> TYPE: PRT
<213> ORGANISM: Homo sapiens

<400> SEQUENCE: 7

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Gly Ala Leu Thr Thr Thr Phe Glu Glu
            180                 185                 190

Leu His Phe Glu Ile Lys Pro His Asp Asp Cys Thr Val Glu Gln Ile
        195                 200                 205

Tyr Glu Ile Leu Lys Ile Tyr Gln Leu Met Asp His Ser Asn Met Asp
```

```
                210             215                 220
Cys Phe Ile Cys Cys Ile Leu Ser His Gly Asp Lys Gly Ile Ile Tyr
225                 230                 235                 240

Gly Thr Asp Gly Gln Glu Ala Pro Ile Tyr Glu Leu Thr Ser Gln Phe
                245                 250                 255

Thr Gly Leu Lys Cys Pro Ser Leu Ala Gly Lys Pro Lys Val Phe Phe
                260                 265                 270

Ile Gln Ala Cys Gln Gly Asp Asn Tyr Gln Lys Gly Ile Pro Val Glu
            275                 280                 285

Thr Asp Ser Glu Glu Gln Pro Tyr Leu Glu Met Asp Leu Ser Ser Pro
290                 295                 300

Gln Thr Arg Tyr Ile Pro Asp Glu Ala Asp Phe Leu Leu Gly Met Ala
305                 310                 315                 320

Thr Val Asn Asn Cys Val Ser Tyr Arg Asn Pro Ala Glu Gly Thr Trp
                325                 330                 335

Tyr Ile Gln Ser Leu Cys Gln Ser Leu Arg Glu Arg Cys Pro Arg Gly
                340                 345                 350

Asp Asp Ile Leu Thr Ile Leu Thr Glu Val Asn Tyr Glu Val Ser Asn
            355                 360                 365

Lys Asp Lys Lys Asn Met Gly Lys Gln Met Pro Gln Pro Thr Phe
370                 375                 380

Thr Leu Arg Lys Lys Leu Val Phe Pro Ser Asp
385                 390                 395

<210> SEQ ID NO 8
<211> LENGTH: 496
<212> TYPE: PRT
<213> ORGANISM: Homo sapiens

<400> SEQUENCE: 8

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Phe His Phe Cys Arg Met Ser Trp Ala Glu
            100                 105                 110

Ala Asn Ser Gln Cys Gln Thr Gln Ser Val Pro Phe Trp Arg Arg Val
        115                 120                 125

Asp His Leu Leu Ile Arg Val Met Leu Tyr Gln Ile Ser Glu Glu Val
    130                 135                 140

Ser Arg Ser Glu Leu Arg Ser Phe Lys Phe Leu Leu Gln Glu Glu Ile
145                 150                 155                 160

Ser Lys Cys Lys Leu Asp Asp Met Asn Leu Leu Asp Ile Phe Ile
                165                 170                 175

Glu Met Glu Lys Arg Val Ile Leu Gly Glu Gly Lys Leu Asp Ile Leu
            180                 185                 190
```

```
Lys Arg Val Cys Ala Gln Ile Asn Lys Ser Leu Leu Lys Ile Ile Asn
            195                 200                 205
Asp Tyr Glu Glu Phe Ser Lys Gly Glu Glu Leu Cys Gly Val Met Thr
        210                 215                 220
Ile Ser Asp Ser Pro Arg Glu Gln Asp Ser Glu Ser Gln Thr Leu Asp
225                 230                 235                 240
Lys Val Tyr Gln Met Lys Ser Lys Pro Arg Gly Tyr Cys Leu Ile Ile
                245                 250                 255
Asn Asn His Asn Phe Ala Lys Ala Arg Glu Lys Val Pro Lys Leu His
            260                 265                 270
Ser Ile Arg Asp Arg Asn Gly Thr His Leu Asp Ala Gly Ala Leu Thr
        275                 280                 285
Thr Thr Phe Glu Glu Leu His Phe Glu Ile Lys Pro His Asp Asp Cys
290                 295                 300
Thr Val Glu Gln Ile Tyr Glu Ile Leu Lys Ile Tyr Gln Leu Met Asp
305                 310                 315                 320
His Ser Asn Met Asp Cys Phe Ile Cys Cys Ile Leu Ser His Gly Asp
                325                 330                 335
Lys Gly Ile Ile Tyr Gly Thr Asp Gly Gln Glu Ala Pro Ile Tyr Glu
            340                 345                 350
Leu Thr Ser Gln Phe Thr Gly Leu Lys Cys Pro Ser Leu Ala Gly Lys
        355                 360                 365
Pro Lys Val Phe Phe Ile Gln Ala Cys Gln Gly Asp Asn Tyr Gln Lys
    370                 375                 380
Gly Ile Pro Val Glu Thr Asp Ser Glu Glu Gln Pro Tyr Leu Glu Met
385                 390                 395                 400
Asp Leu Ser Ser Pro Gln Thr Arg Tyr Ile Pro Asp Glu Ala Asp Phe
                405                 410                 415
Leu Leu Gly Met Ala Thr Val Asn Asn Cys Val Ser Tyr Arg Asn Pro
            420                 425                 430
Ala Glu Gly Thr Trp Tyr Ile Gln Ser Leu Cys Gln Ser Leu Arg Glu
        435                 440                 445
Arg Cys Pro Arg Gly Asp Asp Ile Leu Thr Ile Leu Thr Glu Val Asn
    450                 455                 460
Tyr Glu Val Ser Asn Lys Asp Asp Lys Lys Asn Met Gly Lys Gln Met
465                 470                 475                 480
Pro Gln Pro Thr Phe Thr Leu Arg Lys Lys Leu Val Phe Pro Ser Asp
                485                 490                 495

<210> SEQ ID NO 9
<211> LENGTH: 235
<212> TYPE: PRT
<213> ORGANISM: Homo sapiens

<400> SEQUENCE: 9

Met Asp Phe Ser Arg Asn Leu Tyr Asp Ile Gly Glu Gln Leu Asp Ser
1               5                   10                  15
Glu Asp Leu Ala Ser Leu Lys Phe Leu Ser Leu Asp Tyr Ile Pro Gln
            20                  25                  30
Arg Lys Gln Glu Pro Ile Lys Asp Ala Leu Met Leu Phe Gln Arg Leu
        35                  40                  45
Gln Glu Lys Arg Met Leu Glu Glu Ser Asn Leu Ser Phe Leu Lys Glu
    50                  55                  60
Leu Leu Phe Arg Ile Asn Arg Leu Asp Leu Leu Ile Thr Tyr Leu Asn
65                  70                  75                  80
```

```
Thr Arg Lys Glu Glu Met Glu Arg Glu Leu Gln Thr Pro Gly Arg Ala
                85                  90                  95
Gln Ile Ser Ala Tyr Arg Val Met Leu Tyr Gln Ile Ser Glu Glu Val
            100                 105                 110
Ser Arg Ser Glu Leu Arg Ser Phe Lys Phe Leu Leu Gln Glu Glu Ile
        115                 120                 125
Ser Lys Cys Lys Leu Asp Asp Asp Met Asn Leu Leu Asp Ile Phe Ile
    130                 135                 140
Glu Met Glu Lys Arg Val Ile Leu Gly Glu Gly Lys Leu Asp Ile Leu
145                 150                 155                 160
Lys Arg Val Cys Ala Gln Ile Asn Lys Ser Leu Leu Lys Ile Ile Asn
                165                 170                 175
Asp Tyr Glu Glu Phe Ser Lys Glu Arg Ser Ser Leu Glu Gly Ser
            180                 185                 190
Pro Asp Glu Phe Ser Asn Asp Phe Gly Gln Ser Leu Pro Asn Glu Lys
            195                 200                 205
Gln Thr Ser Gly Ile Leu Ser Asp His Gln Gln Ser Gln Phe Cys Lys
        210                 215                 220
Ser Thr Gly Glu Ser Ala Gln Thr Ser Gln His
225                 230                 235

<210> SEQ ID NO 10
<211> LENGTH: 220
<212> TYPE: PRT
<213> ORGANISM: Homo sapiens

<400> SEQUENCE: 10

Met Asp Phe Ser Arg Asn Leu Tyr Asp Ile Gly Glu Gln Leu Asp Ser
1               5                   10                  15
Glu Asp Leu Ala Ser Leu Lys Phe Leu Ser Leu Asp Tyr Ile Pro Gln
            20                  25                  30
Arg Lys Gln Glu Pro Ile Lys Asp Ala Leu Met Leu Phe Gln Arg Leu
        35                  40                  45
Gln Glu Lys Arg Met Leu Glu Glu Ser Asn Leu Ser Phe Leu Lys Glu
    50                  55                  60
Leu Leu Phe Arg Ile Asn Arg Leu Asp Leu Leu Ile Thr Tyr Leu Asn
65                  70                  75                  80
Thr Arg Lys Glu Glu Met Glu Arg Glu Leu Gln Thr Pro Gly Arg Ala
                85                  90                  95
Gln Ile Ser Ala Tyr Arg Val Met Leu Tyr Gln Ile Ser Glu Glu Val
            100                 105                 110
Ser Arg Ser Glu Leu Arg Ser Phe Lys Phe Leu Leu Gln Glu Glu Ile
        115                 120                 125
Ser Lys Cys Lys Leu Asp Asp Asp Met Asn Leu Leu Asp Ile Phe Ile
    130                 135                 140
Glu Met Glu Lys Arg Val Ile Leu Gly Glu Gly Lys Leu Asp Ile Leu
145                 150                 155                 160
Lys Arg Val Cys Ala Gln Ile Asn Lys Ser Leu Leu Lys Ile Ile Asn
                165                 170                 175
Asp Tyr Glu Glu Phe Ser Lys Asp Phe Gly Gln Ser Leu Pro Asn Glu
            180                 185                 190
Lys Gln Thr Ser Gly Ile Leu Ser Asp His Gln Gln Ser Gln Phe Cys
        195                 200                 205
Lys Ser Thr Gly Glu Ser Ala Gln Thr Ser Gln His
    210                 215                 220
```

-continued

```
            210                 215                 220
```

<210> SEQ ID NO 11
<211> LENGTH: 276
<212> TYPE: PRT
<213> ORGANISM: Homo sapiens

<400> SEQUENCE: 11

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Thr Val Glu Pro
            260                 265                 270

Lys Arg Glu Lys
        275
```

<210> SEQ ID NO 12
<211> LENGTH: 261
<212> TYPE: PRT
<213> ORGANISM: Homo sapiens

<400> SEQUENCE: 12

```
Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
```

```
                        35                  40                  45

Gln Glu Lys Arg Met Leu Glu Glu Ser Asn Leu Ser Phe Leu Lys Glu
             50                  55                  60

Leu Leu Phe Arg Ile Asn Arg Leu Asp Leu Leu Ile Thr Tyr Leu Asn
         65                  70                  75                  80

Thr Arg Lys Glu Glu Met Glu Arg Glu Leu Gln Thr Pro Gly Arg Ala
                         85                  90                  95

Gln Ile Ser Ala Tyr Arg Val Met Leu Tyr Gln Ile Ser Glu Glu Val
                        100                 105                 110

Ser Arg Ser Glu Leu Arg Ser Phe Lys Phe Leu Leu Gln Glu Glu Ile
                    115                 120                 125

Ser Lys Cys Lys Leu Asp Asp Met Asn Leu Leu Asp Ile Phe Ile
                130                 135                 140

Glu Met Glu Lys Arg Val Ile Leu Gly Glu Gly Lys Leu Asp Ile Leu
        145                 150                 155                 160

Lys Arg Val Cys Ala Gln Ile Asn Lys Ser Leu Leu Lys Ile Ile Asn
                        165                 170                 175

Asp Tyr Glu Glu Phe Ser Lys Gly Glu Glu Leu Cys Gly Val Met Thr
                    180                 185                 190

Ile Ser Asp Ser Pro Arg Glu Gln Asp Ser Glu Ser Gln Thr Leu Asp
                195                 200                 205

Lys Val Tyr Gln Met Lys Ser Lys Pro Arg Gly Tyr Cys Leu Ile Ile
            210                 215                 220

Asn Asn His Asn Phe Ala Lys Ala Arg Glu Lys Val Pro Lys Leu His
        225                 230                 235                 240

Ser Ile Arg Asp Arg Asn Gly Thr His Leu Asp Ala Gly Thr Val Glu
                        245                 250                 255

Pro Lys Arg Glu Lys
                    260

<210> SEQ ID NO 13
<211> LENGTH: 538
<212> TYPE: PRT
<213> ORGANISM: Homo sapiens

<400> SEQUENCE: 13

Met Glu Gly Gly Arg Arg Ala Arg Val Val Ile Glu Ser Arg Arg Asn
         1               5                  10                  15

Phe Phe Leu Gly Ala Phe Pro Thr Pro Phe Pro Ala Glu His Val Glu
                     20                  25                  30

Leu Gly Arg Leu Gly Asp Ser Glu Thr Ala Met Val Pro Gly Lys Gly
                     35                  40                  45

Gly Ala Asp Tyr Ile Leu Leu Pro Phe Lys Met Asp Phe Ser Arg
             50                  55                  60

Asn Leu Tyr Asp Ile Gly Glu Gln Leu Asp Ser Glu Asp Leu Ala Ser
         65                  70                  75                  80

Leu Lys Phe Leu Ser Leu Asp Tyr Ile Pro Gln Arg Lys Gln Glu Pro
                         85                  90                  95

Ile Lys Asp Ala Leu Met Leu Phe Gln Arg Leu Gln Glu Lys Arg Met
                        100                 105                 110

Leu Glu Glu Ser Asn Leu Ser Phe Leu Lys Glu Leu Leu Phe Arg Ile
                    115                 120                 125

Asn Arg Leu Asp Leu Leu Ile Thr Tyr Leu Asn Thr Arg Lys Glu Glu
                130                 135                 140
```

-continued

Met Glu Arg Glu Leu Gln Thr Pro Gly Arg Ala Gln Ile Ser Ala Tyr
145                 150                 155                 160

Arg Val Met Leu Tyr Gln Ile Ser Glu Glu Val Ser Arg Ser Glu Leu
                165                 170                 175

Arg Ser Phe Lys Phe Leu Leu Gln Glu Glu Ile Ser Lys Cys Lys Leu
            180                 185                 190

Asp Asp Asp Met Asn Leu Leu Asp Ile Phe Ile Glu Met Glu Lys Arg
        195                 200                 205

Val Ile Leu Gly Glu Gly Lys Leu Asp Ile Leu Lys Arg Val Cys Ala
210                 215                 220

Gln Ile Asn Lys Ser Leu Leu Lys Ile Ile Asn Asp Tyr Glu Glu Phe
225                 230                 235                 240

Ser Lys Glu Arg Ser Ser Leu Glu Gly Ser Pro Asp Glu Phe Ser
                245                 250                 255

Asn Gly Glu Glu Leu Cys Gly Val Met Thr Ile Ser Asp Ser Pro Arg
            260                 265                 270

Glu Gln Asp Ser Glu Ser Gln Thr Leu Asp Lys Val Tyr Gln Met Lys
        275                 280                 285

Ser Lys Pro Arg Gly Tyr Cys Leu Ile Ile Asn Asn His Asn Phe Ala
290                 295                 300

Lys Ala Arg Glu Lys Val Pro Lys Leu His Ser Ile Arg Asp Arg Asn
305                 310                 315                 320

Gly Thr His Leu Asp Ala Gly Ala Leu Thr Thr Thr Phe Glu Glu Leu
                325                 330                 335

His Phe Glu Ile Lys Pro His Asp Asp Cys Thr Val Glu Gln Ile Tyr
            340                 345                 350

Glu Ile Leu Lys Ile Tyr Gln Leu Met Asp His Ser Asn Met Asp Cys
        355                 360                 365

Phe Ile Cys Cys Ile Leu Ser His Gly Asp Lys Gly Ile Ile Tyr Gly
370                 375                 380

Thr Asp Gly Gln Glu Ala Pro Ile Tyr Glu Leu Thr Ser Gln Phe Thr
385                 390                 395                 400

Gly Leu Lys Cys Pro Ser Leu Ala Gly Lys Pro Lys Val Phe Phe Ile
                405                 410                 415

Gln Ala Cys Gln Gly Asp Asn Tyr Gln Lys Gly Ile Pro Val Glu Thr
            420                 425                 430

Asp Ser Glu Glu Gln Pro Tyr Leu Glu Met Asp Leu Ser Ser Pro Gln
        435                 440                 445

Thr Arg Tyr Ile Pro Asp Glu Ala Asp Phe Leu Leu Gly Met Ala Thr
450                 455                 460

Val Asn Asn Cys Val Ser Tyr Arg Asn Pro Ala Glu Gly Thr Trp Tyr
465                 470                 475                 480

Ile Gln Ser Leu Cys Gln Ser Leu Arg Glu Arg Cys Pro Arg Gly Asp
                485                 490                 495

Asp Ile Leu Thr Ile Leu Thr Glu Val Asn Tyr Glu Val Ser Asn Lys
            500                 505                 510

Asp Asp Lys Lys Asn Met Gly Lys Gln Met Pro Gln Pro Thr Phe Thr
        515                 520                 525

Leu Arg Lys Lys Leu Val Phe Pro Ser Asp
        530                 535

<210> SEQ ID NO 14
<211> LENGTH: 216
<212> TYPE: PRT

<213> ORGANISM: Homo sapiens

<400> SEQUENCE: 14

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp
    210                 215

<210> SEQ ID NO 15
<211> LENGTH: 79
<212> TYPE: PRT
<213> ORGANISM: Homo sapiens

<400> SEQUENCE: 15

Asp Phe Ser Arg Asn Leu Tyr Asp Ile Gly Glu Gln Leu Asp Ser Glu
1               5                   10                  15

Asp Leu Ala Ser Leu Lys Phe Leu Ser Leu Asp Tyr Ile Pro Gln Arg
            20                  25                  30

Lys Gln Glu Pro Ile Lys Asp Ala Leu Met Leu Phe Gln Arg Leu Gln
        35                  40                  45

Glu Lys Arg Met Leu Glu Glu Ser Asn Leu Ser Phe Leu Lys Glu Leu
    50                  55                  60

Leu Phe Arg Ile Asn Arg Leu Asp Leu Leu Ile Thr Tyr Leu Asn
65                  70                  75

<210> SEQ ID NO 16
<211> LENGTH: 78
<212> TYPE: PRT
<213> ORGANISM: Homo sapiens

<400> SEQUENCE: 16

Ala Tyr Arg Val Met Leu Tyr Gln Ile Ser Glu Glu Val Ser Arg Ser
1               5                   10                  15

Glu Leu Arg Ser Phe Lys Phe Leu Gln Glu Ile Ser Lys Cys
            20                  25                  30

Lys Leu Asp Asp Met Asn Leu Leu Asp Ile Phe Ile Glu Met Glu
            35                  40                  45

Lys Arg Val Ile Leu Gly Glu Gly Lys Leu Asp Ile Leu Lys Arg Val
50                  55                  60

Cys Ala Gln Ile Asn Lys Ser Leu Leu Lys Ile Ile Asn Asp
65                  70                  75

<210> SEQ ID NO 17
<211> LENGTH: 30
<212> TYPE: PRT
<213> ORGANISM: Homo sapiens

<400> SEQUENCE: 17

Arg Leu Asp Leu Leu Ile Thr Tyr Leu Asn Thr Arg Lys Glu Glu Met
1               5                   10                  15

Glu Arg Glu Leu Gln Thr Pro Gly Arg Ala Gln Ile Ser Ala
            20                  25                  30

<210> SEQ ID NO 18
<211> LENGTH: 479
<212> TYPE: PRT
<213> ORGANISM: Homo sapiens

<400> SEQUENCE: 18

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
    370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Lys Lys Asn Met Gly Lys Gln Met Pro
    450                 455                 460

Gln Pro Thr Phe Thr Leu Arg Lys Lys Leu Val Phe Pro Ser Asp
465                 470                 475

<210> SEQ ID NO 19
<211> LENGTH: 153
<212> TYPE: DNA
<213> ORGANISM: Artificial Sequence
<220> FEATURE:
<223> OTHER INFORMATION: Vector/Fragment 3 Expressed in MIP/NT cells

<400> SEQUENCE: 19
gcccctcagc aagaagccct gcctgatgag acagaggtgg tggaagaaac tgtggcagag      60
gtgactgagg tatctgtggg agctaatcct gtccaggtgg aagtaggaga atttgatgat     120
ggtgcagagg aaaccgaaga ggaggtggtg gcg                                   153

<210> SEQ ID NO 20
<211> LENGTH: 51
<212> TYPE: PRT
<213> ORGANISM: Artificial Sequence
<220> FEATURE:
<223> OTHER INFORMATION: SPARC Polypeptide Expressed in MIP/NT cells

<400> SEQUENCE: 20

Ala Pro Gln Gln Glu Ala Leu Pro Asp Glu Thr Glu Val Val Glu Glu
1               5                   10                  15

Thr Val Ala Glu Val Thr Glu Val Ser Val Gly Ala Asn Pro Val Gln
            20                  25                  30

Val Glu Val Gly Glu Phe Asp Asp Gly Ala Glu Glu Thr Glu Glu Glu

```
                    35                  40                  45
Val Val Ala
    50

<210> SEQ ID NO 21
<211> LENGTH: 256
<212> TYPE: DNA
<213> ORGANISM: Artificial Sequence
<220> FEATURE:
<223> OTHER INFORMATION: Vector/Fragment 2 Expressed in MIP/FS cells

<400> SEQUENCE: 21
gaaaatccct gccagaacca ccactgcaaa cacggcaagg tgtgcgagct ggatgagaac      60
aacaccccca tgtgcgtgtg ccaggacccc accagctgcc cagcccccat tggcgagttt     120
gagaaggtgt gcagcaatga caacaagacc ttcgactctt cctgccactt ctttgccaca     180
aagtgcaccc tggagggcac caagaagggc cacaagctcc acctggacta catcgggcct     240
tgcaaataca tccccc                                                     256

<210> SEQ ID NO 22
<211> LENGTH: 85
<212> TYPE: PRT
<213> ORGANISM: Artificial Sequence
<220> FEATURE:
<223> OTHER INFORMATION: SPARC Polypeptide Expressed in MIP/FS cells

<400> SEQUENCE: 22

Glu Asn Pro Cys Gln Asn His His Cys Lys His Gly Lys Val Cys Glu
1               5                  10                  15

Leu Asp Glu Asn Asn Thr Pro Met Cys Val Cys Gln Asp Pro Thr Ser
            20                  25                  30

Cys Pro Ala Pro Ile Gly Glu Phe Glu Lys Val Cys Ser Asn Asp Asn
        35                  40                  45

Lys Thr Phe Asp Ser Ser Cys His Phe Phe Ala Thr Lys Cys Thr Leu
    50                  55                  60

Glu Gly Thr Lys Lys Gly His Lys Leu His Leu Asp Tyr Ile Gly Pro
65                  70                  75                  80

Cys Lys Tyr Ile Pro
            85

<210> SEQ ID NO 23
<211> LENGTH: 450
<212> TYPE: DNA
<213> ORGANISM: Artificial Sequence
<220> FEATURE:
<223> OTHER INFORMATION: Vector/Fragment 1 Expressed in MIP/EC cells

<400> SEQUENCE: 23
cttgcctgga ctctgagctg accgaattcc ccctgcgcat gcgggactgg ctcaagaacg      60
tcctggtcac cctgtatgag agggatgagg acaacaacct tctgactgag aagcagaagc     120
tgcgggtgaa gaagatccat gagaatgaga agcgcctgga ggcaggagac caccccgtgg     180
agctgctggc ccgggacttc gagaagaact ataacatgta catcttccct gtacactggc     240
agttcggcca gctggaccag caccccattg acgggtacct ctcccacacc gagctggctc     300
cactgcgtgc tcccctcatc cccatggagc attgcaccac ccgctttttc gagacctgtg     360
acctggacaa tgcacaagtac atcgccctgg atgagtgggc cggctgcttc ggcatcaagc     420
agaaggatat cgacaaggat cttgtgatct                                      450
```

```
<210> SEQ ID NO 24
<211> LENGTH: 149
<212> TYPE: PRT
<213> ORGANISM: Artificial Sequence
<220> FEATURE:
<223> OTHER INFORMATION: SPARC Polypeptide Expressed in MIP/EC cells

<400> SEQUENCE: 24

Cys Leu Asp Ser Glu Leu Thr Glu Phe Pro Leu Arg Met Arg Asp Trp
1               5                   10                  15

Leu Lys Asn Val Leu Val Thr Leu Tyr Glu Arg Asp Glu Asp Asn Asn
            20                  25                  30

Leu Leu Thr Glu Lys Gln Lys Leu Arg Val Lys Lys Ile His Glu Asn
        35                  40                  45

Glu Lys Arg Leu Glu Ala Gly Asp His Pro Val Glu Leu Leu Ala Arg
    50                  55                  60

Asp Phe Glu Lys Asn Tyr Asn Met Tyr Ile Phe Pro Val His Trp Gln
65                  70                  75                  80

Phe Gly Gln Leu Asp Gln His Pro Ile Asp Gly Tyr Leu Ser His Thr
                85                  90                  95

Glu Leu Ala Pro Leu Arg Ala Pro Leu Ile Pro Met Glu His Cys Thr
            100                 105                 110

Thr Arg Phe Phe Glu Thr Cys Asp Leu Asp Asn Asp Lys Tyr Ile Ala
        115                 120                 125

Leu Asp Glu Trp Ala Gly Cys Phe Gly Ile Lys Gln Lys Asp Ile Asp
    130                 135                 140

Lys Asp Leu Val Ile
145

<210> SEQ ID NO 25
<211> LENGTH: 283
<212> TYPE: PRT
<213> ORGANISM: Artificial Sequence
<220> FEATURE:
<223> OTHER INFORMATION: Human Procaspase-8 DED domains-containing
      polypeptide

<400> SEQUENCE: 25

Met Glu Gly Gly Arg Arg Ala Arg Val Val Ile Glu Ser Lys Arg Asn
1               5                   10                  15

Phe Phe Leu Gly Ala Phe Pro Thr Pro Phe Pro Ala Glu His Val Glu
            20                  25                  30

Leu Gly Arg Leu Gly Asp Ser Glu Thr Ala Met Val Pro Gly Lys Gly
        35                  40                  45

Gly Ala Asp Tyr Ile Leu Leu Pro Phe Lys Met Asp Phe Ser Arg
    50                  55                  60

Asn Leu Tyr Asp Ile Gly Glu Gln Leu Asp Ser Glu Asp Leu Ala Ser
65                  70                  75                  80

Leu Lys Phe Leu Ser Leu Asp Tyr Ile Pro Gln Arg Lys Gln Glu Pro
                85                  90                  95

Ile Lys Asp Ala Leu Met Leu Phe Gln Arg Leu Gln Glu Lys Arg Met
            100                 105                 110

Leu Glu Glu Ser Asn Leu Ser Phe Leu Lys Glu Leu Leu Phe Arg Ile
        115                 120                 125

Asn Arg Leu Asp Leu Leu Ile Thr Tyr Leu Asn Thr Arg Lys Glu Glu
    130                 135                 140

Met Glu Arg Glu Leu Gln Thr Pro Gly Arg Ala Gln Ile Ser Ala Tyr
```

```
                145                 150                 155                 160
Arg Val Met Leu Tyr Gln Ile Ser Glu Glu Val Ser Arg Ser Glu Leu
                    165                 170                 175

Arg Ser Phe Lys Phe Leu Leu Gln Glu Glu Ile Ser Lys Cys Lys Leu
                180                 185                 190

Asp Asp Asp Met Asn Leu Leu Asp Ile Phe Ile Glu Met Glu Lys Arg
                    195                 200                 205

Val Ile Leu Gly Glu Gly Lys Leu Asp Ile Leu Lys Arg Val Cys Ala
                210                 215                 220

Gln Ile Asn Lys Ser Leu Leu Lys Ile Ile Asn Asp Tyr Glu Glu Phe
225                 230                 235                 240

Ser Lys Glu Arg Ser Ser Leu Glu Gly Ser Pro Asp Glu Phe Ser
                    245                 250                 255

Asn Gly Glu Glu Leu Cys Gly Val Met Thr Ile Ser Asp Ser Pro Arg
                260                 265                 270

Glu Gln Asp Ser Glu Ser Gln Thr Leu Asp Lys
                275                 280
```

<210> SEQ ID NO 26
<211> LENGTH: 187
<212> TYPE: PRT
<213> ORGANISM: Artificial Sequence
<220> FEATURE:
<223> OTHER INFORMATION: Human Procaspase-8 caspase active site-
      containing polypeptide

<400> SEQUENCE: 26

```
Val Tyr Gln Met Lys Ser Lys Pro Arg Gly Tyr Cys Leu Ile Ile Asn
1               5                   10                  15

Asn His Asn Phe Ala Lys Ala Arg Glu Lys Val Pro Lys Leu His Ser
                20                  25                  30

Ile Arg Asp Arg Asn Gly Thr His Leu Asp Ala Gly Ala Leu Thr Thr
            35                  40                  45

Thr Phe Glu Glu Leu His Phe Glu Ile Lys Pro His Asp Asp Cys Thr
        50                  55                  60

Val Glu Gln Ile Tyr Glu Ile Leu Lys Ile Tyr Gln Leu Met Asp His
65                  70                  75                  80

Ser Asn Met Asp Cys Phe Ile Cys Cys Ile Leu Ser His Gly Asp Lys
                85                  90                  95

Gly Ile Ile Tyr Gly Thr Asp Gly Gln Glu Ala Pro Ile Tyr Glu Leu
            100                 105                 110

Thr Ser Gln Phe Thr Gly Leu Lys Cys Pro Ser Leu Ala Gly Lys Pro
        115                 120                 125

Lys Val Phe Phe Ile Gln Ala Cys Gln Gly Asp Asn Tyr Gln Lys Gly
    130                 135                 140

Ile Pro Val Glu Thr Asp Ser Glu Glu Gln Pro Tyr Leu Glu Met Asp
145                 150                 155                 160

Leu Ser Ser Pro Gln Thr Arg Tyr Ile Pro Asp Glu Ala Asp Phe Leu
                165                 170                 175

Leu Gly Met Ala Thr Val Asn Asn Cys Val Ser
            180                 185
```

<210> SEQ ID NO 27
<211> LENGTH: 24
<212> TYPE: DNA
<213> ORGANISM: Artificial Sequence
<220> FEATURE:

```
<223> OTHER INFORMATION: Sense Primer

<400> SEQUENCE: 27
atcacagact ttggacaaag ttta                                              24

<210> SEQ ID NO 28
<211> LENGTH: 24
<212> TYPE: DNA
<213> ORGANISM: Artificial Sequence
<220> FEATURE:
<223> OTHER INFORMATION: Antisense Primer

<400> SEQUENCE: 28
tctgaatcag tctcaacagg tata                                              24

<210> SEQ ID NO 29
<211> LENGTH: 25
<212> TYPE: DNA
<213> ORGANISM: Artificial Sequence
<220> FEATURE:
<223> OTHER INFORMATION: Sense Primer

<400> SEQUENCE: 29
aagcttctga ttattgattc aaacc                                             25

<210> SEQ ID NO 30
<211> LENGTH: 24
<212> TYPE: DNA
<213> ORGANISM: Artificial Sequence
<220> FEATURE:
<223> OTHER INFORMATION: Antisense Primer

<400> SEQUENCE: 30
ttctctatgt ttctcaaaag ttta                                              24

<210> SEQ ID NO 31
<211> LENGTH: 20
<212> TYPE: DNA
<213> ORGANISM: Artificial Sequence
<220> FEATURE:
<223> OTHER INFORMATION: Sense Primer

<400> SEQUENCE: 31
ggacaatgct cacaacgaga                                                   20

<210> SEQ ID NO 32
<211> LENGTH: 20
<212> TYPE: DNA
<213> ORGANISM: Artificial Sequence
<220> FEATURE:
<223> OTHER INFORMATION: Antisense Primer

<400> SEQUENCE: 32
tgttgaccca tttcatcagc                                                   20

<210> SEQ ID NO 33
<211> LENGTH: 24
<212> TYPE: DNA
<213> ORGANISM: Artificial Sequence
<220> FEATURE:
<223> OTHER INFORMATION: Sense Primer

<400> SEQUENCE: 33
tgtgcagcat ttaacgtcat atgt                                              24
```

```
<210> SEQ ID NO 34
<211> LENGTH: 19
<212> TYPE: DNA
<213> ORGANISM: Artificial Sequence
<220> FEATURE:
<223> OTHER INFORMATION: Antisense Primer

<400> SEQUENCE: 34
acgcagcttg agttcagaa                                                   19

<210> SEQ ID NO 35
<211> LENGTH: 21
<212> TYPE: DNA
<213> ORGANISM: Artificial Sequence
<220> FEATURE:
<223> OTHER INFORMATION: Sense Primer

<400> SEQUENCE: 35
tttgagttgc atcctagccc a                                                21

<210> SEQ ID NO 36
<211> LENGTH: 18
<212> TYPE: DNA
<213> ORGANISM: Artificial Sequence
<220> FEATURE:
<223> OTHER INFORMATION: Antisense Primer

<400> SEQUENCE: 36
gctggtgagc tcgttctc                                                    18

<210> SEQ ID NO 37
<211> LENGTH: 17
<212> TYPE: DNA
<213> ORGANISM: Artificial Sequence
<220> FEATURE:
<223> OTHER INFORMATION: Sense Primer

<400> SEQUENCE: 37
gccacggctg cttccag                                                     17

<210> SEQ ID NO 38
<211> LENGTH: 16
<212> TYPE: DNA
<213> ORGANISM: Artificial Sequence
<220> FEATURE:
<223> OTHER INFORMATION: Antisense Primer

<400> SEQUENCE: 38
ggcgtacagg tctttc                                                      16

<210> SEQ ID NO 39
<211> LENGTH: 50
<212> TYPE: DNA
<213> ORGANISM: Artificial Sequence
<220> FEATURE:
<223> OTHER INFORMATION: Forward Primer

<400> SEQUENCE: 39
tctttagaaa tactataacc aggtaccatc aggtaccgtg tagaccggag                 50

<210> SEQ ID NO 40
<211> LENGTH: 30
<212> TYPE: DNA
<213> ORGANISM: Artificial Sequence
<220> FEATURE:
<223> OTHER INFORMATION: Reverse Primer
```

-continued

```
<400> SEQUENCE: 40
ggttatagta tttctaaaga cgacttcagg                                   30

<210> SEQ ID NO 41
<211> LENGTH: 35
<212> TYPE: DNA
<213> ORGANISM: Artificial Sequence
<220> FEATURE:
<223> OTHER INFORMATION: Forward Primer

<400> SEQUENCE: 41
ttgacctgtc acttctagaa atagcggagt tcaag                             35

<210> SEQ ID NO 42
<211> LENGTH: 28
<212> TYPE: DNA
<213> ORGANISM: Artificial Sequence
<220> FEATURE:
<223> OTHER INFORMATION: Reverse Primer

<400> SEQUENCE: 42
tctagaagtg acaggtcaac aaggggtt                                     28

<210> SEQ ID NO 43
<211> LENGTH: 50
<212> TYPE: DNA
<213> ORGANISM: Artificial Sequence
<220> FEATURE:
<223> OTHER INFORMATION: Forward Primer

<400> SEQUENCE: 43
gagatagtct aaagtcttct cctagtacag gagctaactc ccagaaaatt             50

<210> SEQ ID NO 44
<211> LENGTH: 29
<212> TYPE: DNA
<213> ORGANISM: Artificial Sequence
<220> FEATURE:
<223> OTHER INFORMATION: Reverse Primer

<400> SEQUENCE: 44
agaagacttt agctatctcg tactgggac                                    29
```